United States Patent
Marti et al.

(10) Patent No.: US 9,499,499 B2
(45) Date of Patent: *Nov. 22, 2016

(54) VALSARTAN SALTS

(71) Applicants: Erwin Marti, Basel (CH); Hans Rudolf Oswald, Starrkirch-Wil (CH); Peter Buehlmayer, Arlesheim (CH); Wolfgang Marterer, Bad Krozingen (DE)

(72) Inventors: Erwin Marti, Basel (CH); Hans Rudolf Oswald, Starrkirch-Wil (CH); Peter Buehlmayer, Arlesheim (CH); Wolfgang Marterer, Bad Krozingen (DE)

(73) Assignee: Novartis AG, Basel (CH)

( * ) Notice: Subject to any disclaimer, the term of this patent is extended or adjusted under 35 U.S.C. 154(b) by 364 days.

This patent is subject to a terminal disclaimer.

(21) Appl. No.: 14/081,441

(22) Filed: Nov. 15, 2013

(65) Prior Publication Data

US 2014/0073677 A1  Mar. 13, 2014

Related U.S. Application Data

(60) Division of application No. 13/599,032, filed on Aug. 30, 2012, now abandoned, which is a continuation of application No. 12/186,172, filed on Aug. 5, 2008, now Pat. No. 8,278,339, which is a continuation of application No. 11/678,284, filed on Feb. 23, 2007, now abandoned, which is a continuation of application No. 10/333,100, filed as application No. PCT/EP01/08253 on Jul. 17, 2001, now abandoned.

(30) Foreign Application Priority Data

Jul. 19, 2000 (EP) ..................... 00115556

(51) Int. Cl.
| | | |
|---|---|---|
| A61K 31/00 | (2006.01) | |
| C07D 257/04 | (2006.01) | |
| A61K 45/06 | (2006.01) | |
| A61K 31/41 | (2006.01) | |

(52) U.S. Cl.
CPC ............. *C07D 257/04* (2013.01); *A61K 31/41* (2013.01); *A61K 45/06* (2013.01)

(58) Field of Classification Search
CPC ...... A61K 31/00; A61K 45/06; A61K 31/41; C07D 257/04
USPC ................ 514/381, 16.2, 15.8, 869; 548/253
See application file for complete search history.

(56) References Cited

U.S. PATENT DOCUMENTS

| 4,499,017 A | 2/1985 | Pirie |
| 5,330,978 A | 7/1994 | Wakimasu |
| 5,399,578 A | 3/1995 | Buhlmayer |
| 5,965,592 A | 10/1999 | Buhlmayer |
| 6,071,931 A | 6/2000 | Humke |

FOREIGN PATENT DOCUMENTS

| EP | 0443983 A1 | 8/1991 | |
| WO | 95/24901 A1 | 9/1995 | |
| WO | 96/31234 A1 | 10/1996 | |
| WO | WO 9631234 A1 * | 10/1996 | ........... A61K 38/556 |
| WO | 97/13513 A1 | 4/1997 | |
| WO | 97/49394 A2 | 12/1997 | |
| WO | 99/11260 A1 | 3/1999 | |
| WO | 99/67231 A1 | 12/1999 | |
| WO | 00/59475 A1 | 10/2000 | |
| WO | 02/06253 A1 | 1/2002 | |

OTHER PUBLICATIONS

Burns KD, Angiotensin II and its receptors in the diabetic Kidney, Am J Kidney Dis. Sep. 2000;36(3):449-67.*
Cheronis's publication, "Semimicro Experimental Organic Chemistry", 1958, chapter 5.*
Kano et al: "A HNG-CoA reductase inhibitor improved regression of atherosclerosis in the rabbit aorta without affecting serum lipid levels: possible relevance of up-relation of endothelia no synthase mRNA", Biochemical and Biophysical Research Communications, No. 259, pp. 414-419 (1999).
Stout George H. et al: University of Washington X-ray structure determination, a practical guide chapter 3, symmetry operations and space groups, pp. 38-61 (1968).
Berge et al: "Pharmaceutical Salts", J. Pharm. Sci., vol. 66, No. 1, pp. 1-19 (1977).
Spurlock, "Increasing solutbility of enoxacin and nofloxacin by means of salt formation", J. Parenter. Sci. Technol. vol. 40, No. 2, pp. 70-72 (1986).
Jeremic et al: "Effects of a new angiotension-converting enzyme inhibitor (Idrapil) in rats with left ventricular dysfunction after myocardial infarction", Journal of Cardiovascular Phamrmacology, No. 27, pp. 347-354 (1996).
Cheronis: "Semimicro experimental organic chemistry", Hadrian Press, Inc., New York, Chapter 5, pp. 31-49 (1958).
Cohen et al: "Protective effects of CGS 30440, a combined angiotensin-converting enzyme inhibitor and neutral endopeptidase inhibitor, in a model of chronic renal failure", Journal of Cardiovascular Pharmacology, No. 32, pp. 87-95 (1998).
Jiang et al: Endothelium-independent relaxation of rabbit coronary artery by 17beta-Oestradiol in vitro, J. Pharmacol, No. 104, pp. 1033-1037 (1991).

* cited by examiner

Primary Examiner — Michael G Hartley
Assistant Examiner — Nabila Ebrahim
(74) Attorney, Agent, or Firm — David Kurlandsky

(57) ABSTRACT

The invention relates to new salts of valsartan or crystalline, also partly crystalline and amorphous salts of valsartan, the respective production and usage, and pharmaceutical preparations containing such a salt.

5 Claims, No Drawings

VALSARTAN SALTS

The invention relates to new salts of the $AT_1$ receptor antagonist (S)—N-(1-carboxy-2-methyl-prop-1-yl)-N-pentanoyl-N-[2'-(1H-tetrazol-5-yl)-biphenyl-4-yl-methyl]-amine (valsartan) of formula

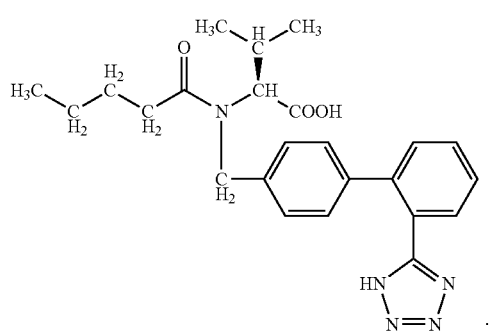

The active ingredient valsartan is the free acid which is described specifically in EP 0443983, especially in example 16; it has two acidic hydrogen atoms: (i) the hydrogen atom (H atom) of the carboxyl group, and (ii) that of the tetrazole ring. Accordingly, one acidic H atom (primarily the carboxyl H atom) or both acidic H atoms may be replaced by a monovalent or higher valent, e.g. divalent, cation. Mixed salts may also be formed.

EP 443983 does not disclose any specific salts of valsartan. Also, it does not mention any special properties of salts. Meanwhile, the active ingredient valsartan has been introduced as an anti-hypertensive agent in a series of countries under the trade name DIOVAN.

The free acid valsartan has a melting point in a closed crucible of 80 to 95° C. and in an open crucible of 105 to 110° C. and a melting enthalpy of 12 kJ/mol. The optical rotation is $[\alpha]^{20}_D=(-70\pm2)°$ for a concentration of c=1% in methanol.

The density of the valsartan crystals and of the salt hydrates was determined by a helium pycnometer (Accupyc 1330 of Micromeritics, Norcross, Ga., USA). The density for the crystals of the free acid valsartan is 1.20±0.02.

The X-ray diffraction diagram consists essentially of a very broad, diffuse Xray reflection; the free acid is therefore characterised as almost amorphous under X-ray. The melting point linked with the measured melting enthalpy of 12 kJ/mol unequivocally confirm the existence of a considerable residual arrangement in the particles or structural domains for the free acid valsartan.

There is a need for more stable, e.g. crystalline forms of valsartan, which are even easier to manage in the drying or grinding processes following the final stage of the chemical preparation process and also in the steps for preparing the pharmaceutical formulations. Many futile attempts have been made to find improved forms through salt formation, the forms ideally being as crystalline as possible, as well as physically and chemically stable. Only the salts according to the invention, their solvates and polymorphous forms thereof exhibit the desired improved properties.

The formation of salts of valsartan with the desired advantageous properties has proved to be difficult. In the majority of cases, for example, amorphous salts with little stability are obtained (such as hard foams, waxes or oils). Extensive research has shown that the salts of valsartan according to the invention have proved to be particularly advantageous compared with the free acid valsartan.

The objects of the present invention are salts of valsartan which are selected from the group consisting of the mono-sodium salt, the monopotassium salt, the dipotassium salt, the magnesium salt, the calcium salt, the bis-diethylammonium salt, the bis-dipropylammonium salt, the bis-dibutylammonium salt, the mono-L-arginine salt, the bis-L-arginine salt, the mono-L-lysine salt and the bis-L-lysine salt, as well as salt mixtures, or respectively, an amorphous form, a solvate, especially hydrate, as well as a polymorphous form thereof, the respective production and usage, and pharmaceutical preparations containing such salts.

The objects of the present invention are salts of valsartan which are selected from the group consisting of the mono-sodium salt, the monopotassium salt, the dipotassium salt, the magnesium salt, the calcium salt, the bis-diethylammonium salt, the bis-dipropylammonium salt, the bis-dibutylammoniumsalt, the mono-L-arginine salt, the bis-L-arginine salt, the mono-L-lysine salt and the bis-L-lysine salt, or respectively, an amorphous form, a solvate, especially hydrate, as well as a polymorphous form thereof.

Salt mixtures are (i) single salt forms from different cations selected from the above group or (ii) mixtures of those single salt forms which exist for example in the form of conglomerates.

Preferred salts are for example selected from the mono-sodium salt in amorphous form;
di-sodium salt of valsartan in amorphous or crystalline form, especially in hydrate form, thereof. Mono-potassium salt of valsartan in amorphous form;
di-potassium salt of valsartan in amorphous or crystalline form, especially in hydrate form, thereof.
calcium salt of valsartan in crystalline form, especially in hydrate form, primarily the tetrahydrate thereof;
magnesium salt of valsartan in crystalline form, especially in hydrate form, primarily the hexahydrate thereof;
calcium/magnesium mixed salt of valsartan in crystalline form, especially in hydrate form;
bis-diethylammonium salt of valsartan in crystalline form, especially in hydrate form;
bis-dipropylammonium salt of valsartan in crystalline form, especially in hydrate form;
bis-dibutylammonium salt of valsartan in crystalline form, especially in hydrate form, primarily the hemihydrate thereof;
mono-L-arginine salt of valsartan in amorphous form;
bis-L-arginine salt of valsartan in amorphous form;
mono-L-lysine salt of valsartan in amorphous form;
bis-L-lysine salt of valsartan in amorphous form.

The salts according to the invention preferably exist in isolated and essentially pure form, for example in a degree of purity of >95%, preferably >98%, primarily >99%. The enantiomer purity of the salts according to the invention is >98%, preferably >99%.

Compared with the free acid, the salts according to the invention, or the amorphous forms, solvates such as salt hydrates, and also the corresponding polymorphous forms thereof, have unexpectedly advantageous properties. Under given conditions, the crystalline salts and crystalline salt hydrates have a clear melting point which is linked with a marked, endothermic melting enthalpy. The crystalline salts according to the invention are stable and are of better quality than valsartan also during storage and distribution. The amorphous or partially amorphous salts have limited stability, i.e. as the solid, they have a restricted stability range. To be stabilised, they require certain measures which can be achieved for example by galenic formulations.

In addition, both the crystalline and the amorphous salts according to the invention have a high degree of dissociation in water and thus substantially improved water solubility. These properties are of advantage, since on the one hand the dissolving process is quicker and on the other hand a smaller amount of water is required for such solutions. Furthermore, the higher water solubility can, under certain conditions, also lead to increased biological availability of the salts or salt hydrates in the case of solid dosage forms. Improved properties are beneficial especially to the patients. Furthermore, some of the salts according to the invention have proved to be exceptionally physically stable, particularly the alkaline earth salts. For different relative humidities at room temperature and also at a slightly higher temperatures, the salt hydrates according to the invention show practically no water absorption or water loss over a wide range of humidities and for periods of a few hours, e.g. four hours. Also, for example, the melting point of the salts according to the invention will not be changed by storing under different relative humidities.

Improved physicochemical properties of certain salts or certain salt hydrates are of great importance both when they are produced as a pharmaceutically active substance and when producing, storing and applying the galenic preparation. In this way, starting with improved constancy of the physical parameters, an even higher quality of the formulations can be guaranteed. The high stability of the salts or salt hydrates also give the possibility of attaining economic advantages by enabling simpler process steps to be carried out during working up. The high crystallinity of certain salt hydrates allows the use of a choice of analytical methods, especially the various X-ray methods, the usage of which permits a clear and simple analysis of their release to be made. This factor is also of great importance to the quality of the active substance and its galenic forms during production, storage and administration to the patients. In addition, complex provisions for stabilising the active ingredient in the galenic formulations can be avoided.

The invention accordingly relates to crystalline, also partly crystalline and amorphous salts of valsartan.

As well as the solvates, such as hydrates, the invention also relates to polymorphous forms of the salts according to the invention.

Solvates and also hydrates of the salts according to the invention may be present, for example, as hemi-, mono-, di-, tri-, tetra-, penta-, hexa-solvates or hydrates, respectively. Solvents used for crystallisation, such as alcohols, especially methanol, ethanol, aldehydes, ketones, especially acetone, esters, e.g. ethyl acetate, may be embedded in the crystal grating. The extent to which a selected solvent or water leads to a solvate or hydrate in crystallisation and in the subsequent process steps or leads directly to the free acid is generally unpredictable and depends on the combinations of process conditions and the various interactions between valsartan and the selected solvent, especially water. The respective stability of the resulting crystalline or amorphous solids in the form of salts, solvates and hydrates, as well as the corresponding salt solvates or salt hydrates, must be determined by experimentation. It is thus not possible to focus solely on the chemical composition and the stoichiometric ratio of the molecules in the resulting solid, since under these circumstances both differing crystalline solids and differing amorphous substances may be produced.

The description salt hydrates for corresponding hydrates may be preferred, as water molecules in the crystal structure are bound by strong intermolecular forces and thereby represent an essential element of structure formation of these crystals which, in part, are extraordinarily stable. However, water molecules are also existing in certain crystal lattices which are bound by rather weak intermolecular forces. Such molecules are more or less integrated in the crystal structure forming, but to a lower energetic effect. The water content in amorphous solids can, in general, be clearly determined, as in crystalline hydrates, but is heavily dependent on the drying and ambient conditions. In contrast, in the case of stable hydrates, there are clear stoichiometric ratios between the pharmaceutical active substance and the water. In many cases these ratios do not fulfil completely the stoichiometric value, normally it is approached by lower values compared to theory because of certain crystal defects. The ratio of organic molecules to water molecules for the weaker bound water may vary to a considerable extend, for example, extending over di-, tri- or tetra-hydrates. On the other hand, in amorphous solids, the molecular structure classification of water is not stoichiometric; the classification may however also be stoichiometric only by chance.

In some cases, it is not possible to classify the exact stoichiometry of the water molecules, since layer structures form, e.g. in the alkali metal salts, especially in the potassium salt, so that the embedded water molecules cannot be determined in defined form.

For the crystalline solids having identical chemical composition, the different resulting crystal gratings are summarised by the term polymorphism.

Any reference hereinbefore and hereinafter, to the salts according to the invention is to be understood as referring also to the corresponding solvates, such as hydrates, and polymorphous modifications, and also amorphous forms, as appropriate and expedient.

Especially preferred are the tetrahydrate of the calcium salt of valsartan and the hexahydrate of the magnesium salt of valsartan.

The X-ray diffraction diagram of powders of these two salt hydrates has a number of discrete X-ray reflections, and practically no signs of non-crystalline or amorphous portions. The degree of crystallisation of these defined salt hydrates is therefore surprisingly high. Equally, relatively large crystals may be cultured from certain salt hydrates, and in the crystallographic sense these are single crystals. Such single crystals allow the structure of the solid to be determined. It is effected by computer-aided evaluation of the reflection intensities measured by an X-ray diffractometer.

This process for determining the structure of a crystal enables, under normal conditions such as high physical, chemical and enantiomeric purity of the gauged crystals, a clear determination of the structure to be carried out on a molecular or atomic level, namely symmetry and size of the elementary cells, atom positions and temperature factors, and from the ascertained cell volume, the X-ray-photographic density is shown on the basis of a molecular weight. At the same time, the X-ray-photographic structure determination supplies details of its quality.

The outstanding properties of these two salt hydrates are based on the crystals, which form these salts by incorporating four or six water molecules per valsartan molecule. Thus, practically perfect three-dimensional crystal gratings are produced. These two salts have water solubility that is several times better than the free acid of valsartan, and this is especially surprisingly at high melting points and melting enthalpies, which are eight or five times greater than the free acid. The extraordinary crystal gratings of these two salt hydrates are the basis for the chemical and physical stability of these two compounds.

The particularly notable salt hydrate is the tetrahydrate of the calcium salt of valsartan. In a closed specimen container, for a heating rate of $T_r=10$ K·min$^{-1}$ it has a melting point of 205±1.5° C. and a melting enthalpy of 98±4 kJ·Mol$^{-1}$. The tetrahydrate of the calcium salt of valsartan is not stable at elevated temperatures both in respect of the hydrate water and in respect of the structure of the molecule. The indicated melting point is a hydrate melting point which can only be measured in a closed specimen container. Gold containers with a wall thickness of 0.2 mm were used; after weighing in samples of between 2 and 4 mg salt hydrate, they were sealed by cold welding. These gold containers have an internal free volume of ca. 22 microliters. The amounts of the sample and the volume of the pressurised containers must be suitably adapted, so that strong dehydration of the salt hydrates cannot take place during measurement of the melting point. The partial pressure of the water at 205° Celsius is ca. 18 bar, so that with an open container in DSC (Differential Scanning calorimeter) during measurement of the melting point, conversion to the anhydrate takes place. If the data from several heating rates ($T_r=10$, 20, 40 K·min$^{-1}$) are extrapolated to a continuously rapid heating rate, a melting point of 213±2° C. and a melting enthalpy of 124±5 kJ·Mol$^{-1}$ result. Both the high hydrate melting point and the amount of the melting enthalpy are an expression of the exceptional stability of the crystal grating of the tetrahydrate of the calcium salt of valsartan. These two thermodynamic characteristics illustrate the advantageous physical properties, compared to the free acid, with the two corresponding data, namely a melting point in the closed system of 90° C. and a melting enthalpy of 12 kJ·Mol$^{-1}$. These thermodynamic data, together with the X-ray data, prove the high stability of this crystal grating. They are the foundation for the special physical and chemical resistance of the tetrahydrate of the calcium salt of valsartan.

A measurement of the infrared absorption spectrum of the tetrahydrate of the calcium salt of valsartan in a potassium bromide compressed tablet shows the following significant bands expressed in reciprocal wave numbers (cm$^{-1}$): 3750-3000 (st); 3400-2500 (st); 1800-1520 (st); 1500-1380 (st); 1380-1310 (m); 1290-1220 (w); 1220-1190 (w); 1190-1160 (w); 1160-1120 (w); 1120-1050 (w); 1030-990 (m); 989-960 (w), 950-920 (w); 780-715 (m); 710-470 (m). The intensities of the absorption bands are indicated as follows: (w)=weak; (m)=medium; and (st)=strong intensity. Measurement of the infrared spectrum likewise took place by means of ATR-IR (Attenuated Total Reflection-Infrared Spectroscopy) using the instrument Spektrum BX from Perkin-Elmer Corp., Beaconsfield, Bucks, England.

The tetrahydrate of the calcium salt of valsartan has the following absorption bands expressed in reciprocal wave numbers (cm$^{-1}$):
3594 (w); 3306 (w); 3054 (w); 2953 (w); 2870 (w); 1621 (st); 1578 (m); 1458 (m); 1441 (m); 1417 (m); 1364 (m); 1336 (w); 1319 (w); 1274 (w); 1241 (w); 1211 (w); 1180 (w); 1149 (w); 1137 (w); 1106 (w); 1099 (w); 1012 (m); 1002 (w); 974 (w); 966 (w); 955 (w); 941 (w); 863 (w); 855 (w); 844 (w); 824 (w); 791 (w); 784 (w); 758 (m); 738 (m); 696 (m); 666 (m).

The intensities of the absorption bands are indicated as follows: (w)=weak; (m)=medium and (st)=strong intensity.

The most intensive absorption bands of the ATR-IR spectroscopy are shown by the following values expressed in reciprocal wave numbers (cm$^{-1}$): 3306 (w); 1621 (st); 1578 (m); 1458 (m); 1441 (m); 1417 (m); 1364 (m); 1319 (w); 1274 (w); 1211 (w); 1180 (w); 1137 (w); 1012 (m); 1002 (w); 758 (m); 738 (m); 696 (m); 666 (m).

The error margin for all absorption bands of ATR-IR is ±2 cm$^{-1}$.

The water content is in theory 13.2% for the tetrahydrate of the calcium salt of valsartan. Using the thermo-scale TGS-2 (Perkin-Elmer Corp., Norwalk, Conn. USA) the water content was determined as 12.9%. A total formula was calculated from this $(C_{24}H_{27}N_5O_3)^{2-}Ca^{2+} \cdot (3.9\pm0.1) H_2O$.

Using thermogravimetry, in a water-free $N_2$ atmosphere, the weight loss, i.e. the water loss for the tetrahydrate as a function of temperature, was measured at a heating rate of 10 K·min$^{-1}$. The results are illustrated in table 1.

TABLE 1

| temperature [° C.] | weight loss or water loss in % |
| --- | --- |
| 25 | 0 |
| 50 | 0 |
| 75 | 0.5 |
| 100 | 3.5 |
| 125 | 10.2 |
| 150 | 12.4 |
| 175 | 12.8 |
| 200 | 12.9 |
| 225 | 12.9 |
| 250 | 13.0 |
| 275 | 13.2 |

The solubility of the tetrahydrate of the calcium salt of valsartan in water-ethanol mixtures is illustrated in Table 2 for a temperature of 22° C.

TABLE 2

| vol-% ethanol in water | solubility of the tetrahydrate of the calcium salt of valsartan in g/l solution at 22° C. |
| --- | --- |
| 0 | 9 (pH = 7.4) |
| 10 | 9 |
| 30 | 14 |
| 50 | 46 |

A comparison of the solubilities of the two most important salts according to the invention and the free acid in distilled water is illustrated in Table 3.

TABLE 3

| Compound | solubility in g/l solution at 22° C. |
| --- | --- |
| valsartan | 0.17 |
| tetrahydrate of the calcium salt of valsartan | 9 |
| hexahydrate of the magnesium salt of valsartan | 59 |

Further characterisation of the tetrahydrate of the calcium salt of valsartan is effected using the interlattice plane intervals determined by a X-ray powder pattern. Measurement of the X-ray powder patterns was made with a Guinier camera (FR 552 from Enraf Nonius, Delft, NL) on an X-ray film in transmission geometry, using Cu-Ka$_1$ radiation at room temperature. Evaluation of the films for calculation of the interlattice plane intervals is made both visually and by a Line-Scanner (Johansson Täby, S), and the reflection intensities are determined simultaneously. The preferred characterisation of the tetrahydrate of the calcium salt of valsartan is obtained from the interlattice plane intervals d of the ascertained X-ray diffraction diagrams, whereby, in the following, average values are indicated with the appropriate error limits.

d in [Å]: 16.1±0.3, 9.9±0.2, 9.4±0.2, 8.03±0.1, 7.71±0.1, 7.03±0.1, 6.50±0.1, 6.33±0.1, 6.20±0.05, 5.87±0.05, 5.74±0.05, 5.67±0.05, 5.20±0.05, 5.05±0.05, 4.95±0.05, 4.73±0.05, 4.55±0.05, 4.33±0.05, 4.15±0.05, 4.12±0.05, 3.95±0.05, 3.91±0.05, 3.87±0.05, 3.35±0.05.

The most intensive reflections in the X-ray diffraction diagram show the following interlattice plane intervals:

d in [Å]: 16.1±0.3, 9.9±0.2, 9.4±0.2, 7.03±0.1, 6.50±0.1, 5.87±0.05, 5.74±0.05, 4.95±0.05, 4.73±0.05, 4.33±0.05, 4.15±0.05, 4.12±0.05, 3.95±0.05.

A preferred method of checking the above-indicated average values of the interlattice plane intervals and intensities measured by experimentation from X-ray diffraction diagrams with a Guinier camera, for a given substance, consists in calculating these intervals and their intensities from the comprehensive single crystal structure determination. This structure determination yields cell constants and atom positions, which enable the X-ray diffraction diagram corresponding to the solid to be calculated by means of computer-aided calculation methods (programme CaRine Crystallography, Université de Compiègne, France). A comparison of these data, namely the interlattice plane intervals and intensities of the most important lines of the tetrahydrate of the calcium salt of valsartan, obtained from measurements with the Guinier camera and from calculating the single crystal data, is illustrated in Table 4.

TABLE 4

| measured | | calculated | |
|---|---|---|---|
| d in [Å] | Intensity | d in [Å] | Intensity |
| 16.10 | very strong | 16.02 | very strong |
| 9.89 | strong | 9.88 | very strong |
| 9.38 | average | 9.37 | average |
| 8.03 | weak | 8.02 | average |
| 7.71 | weak | 7.70 | weak |
| 7.03 | average | 7.01 | average |
| 6.50 | average | 6.49 | average |
| 6.33 | weak | 6.33 | weak |
| 6.20 | very weak | 6.19 | very weak |
| 5.87 | average | 5.862 | average |
| 5.74 | average | 5.738 | average |
| 5.67 | very weak | 5.658 | very weak |
| 5.20 | very weak | 5.199 | very weak |
| 5.05 | very weak | 5.040 | very weak |
| 4.95 | average | 4.943 | weak |
| 4.73 | weak | 4.724 | weak |
| 4.55 | weak | 4.539 | weak |
| 4.33 | weak | 4.338 | weak |
| 4.15 | strong | 4.150 | strong |
| 4.12 | weak | 4.114 | weak |
| 3.95 | average | 3.941 | average |
| 3.35 | weak | 3.349 | weak |

The invention relates to the crystalline tetrahydrate of the calcium salt of (S)—N-(1-carboxy-2-methylprop-1-yl)-N-pentanoyl-N-[2'-(1H-tetrazol-5-yl)biphenyl-4-ylmethyl]-amine, a crystalline solid which is clearly characterised by the data and parameters obtained from single crystal X-ray analysis and X-ray powder patterns. An in-depth discussion of the theory of the methods of single crystal X-ray diffraction and the definition of the evaluated crystal data and the parameters may be found in Stout & Jensen, X-Ray Structure Determination; A Practical Guide, Mac Millian Co., New York, N.Y. (1968) chapter 3.

The data and parameters of the single crystal X-ray structure determination for the tetrahydrate of the calcium salt of valsartan are contained in Table 5.

TABLE 5

Crystal data and parameters of the tetrahydrate of the calcium salt of valsartan

| Crystal data | |
|---|---|
| sum formula | $(C_{24}H_{27}N_5O_3)^{2-} \cdot Ca^{2+} \cdot 4\ H_2O$ |
| molecular mass | 545.65 |
| crystal colour | colourless |
| crystal shape | flat prisms |
| crystal system | monoclinic |
| space group | $P2_1$ |
| size of the single crystal | $0.42 \cdot 0.39 \cdot 0.17$ mm$^3$ |
| dimensions and angle of elementary cell | a = 10.127(2) Å |
| | b = 8.596(2) Å |
| | c = 32.214(6) Å |
| | α = 90° |
| | β = 95.34(3)° |
| | γ = 90° |
| volume of elementary cell | $V_c = 2792.1(10)$ Å$^3$ |
| number of molecules in the elementary cell | 4 |
| F (000) | 1160 |
| measurement range of cell parameters (Θ) | 7.47-16.50° |
| calculated density | 1.298 (g · cm$^{-3}$) |
| linear absorption coefficient | 0.274 mm$^{-1}$ |
| X-ray measurement data | |
| diffractometer | Enraf Nonius CAD4 |
| X-radiation (graphite monochromator) | MoKα |
| wavelength | 0.71073 |
| temperature | 295 K |
| scan range (θ) | 1.27-31.99° |
| scan mode | ω/2 Θ |
| reflections collected/unique | 19384/18562 |
| number of significant reflections (I > 2σ(I)) | 10268 |
| variation in intensity | 1.7% |
| absorption correction | numeric |
| Structure refinement | |
| method | full matrix, least squares, F$^2$ |
| number of parameters | 893 |
| agreement index (R) | 6.2% |
| weighted agreement index (R$_W$) | 14.4% |
| S factor (Goodness of fit) | 1.085 |
| number of reflections used | 18562 |
| treatment of all hydrogen atoms in the molecule, including in the water molecules | all found by difference-Fourier calculation, almost all isotropically refined, a few theoretically fixed (riding) |
| extinction correction | none |
| maximum/minimum residual electron density in conclusive difference-Fourier calculation | 0.662/−0.495 (e · Å$^{-3}$) |
| absolute structure parameters | 0.00 (4) |

Computer programmes used
SHELXS 86 (Sheldrick, Göttingen, 1990)
SHELXL 96 (Sheldrick, Göttingen, 1996)
SCHAKAL 86 (Keller, Freiburg 1986)
PLATON (Spek, Acta Cryst., 1990)

The elementary cell is defined by six parameters, namely by the grating constants a, b and c, and by the axial angle, namely by α, β, and γ. In this way, the volume of the elementary cell $V_c$ is determined. A differentiated description of these crystal parameters is illustrated in chapter 3 of Stout & Jensen (see above). The details for the tetrahydrate of the calcium salt of valsartan from the single crystal measurements, especially the atom coordinates, the isotropic thermal parameters, the coordinates of the hydrogen atoms as well as the corresponding isotropic thermal parameters, show that a monoclinic elementary cell exists, its cell content of four formula units $Ca^{2+}$ valsartan$^{2-}$.$4H_2O$ occurring as a result of two crystallographic independent units on two-fold positions.

Given the acentric space group $P2_1$ determined from the single crystal X-ray structure determination, a racemate is ruled out. Thus the enantiomeric purity of the S-configuration for the crystalline tetrahydrate of the calcium salt of (S)—N-(1-carboxy-2-methylprop-1-yl)-N-pentanoyl-N-[2'-(1H-tetrazol-5-yl)biphenyl-4-ylmethyl]-amine is verified.

An essential feature for the quality of a pure active substance both for the physical-chemical procedures such as drying, sieving, grinding, and in the galenic processes which are carried out with pharmaceutical excipients, namely in mixing processes, in granulation, in spray-drying, in tabletting, is the water absorption or water loss of this active substance depending on temperature and the relative humidity of the environment in question. With certain formulations, free and bound water is without doubt introduced with excipients and/or water is added to the process mass for reasons associated with the respective formulation process. In this way, the pharmaceutical active substance is exposed to free water over rather long periods of time, depending on the temperature of the different activity (partial vapour pressure).

A clear characterisation of this property is achieved by means of isothermal measurements over predetermined time intervals and predetermined relative humidity using dynamic vapour sorption (DVS-1 from the company Surface Measurement Systems LTD, Marlow, Buckinghamshire, UK). Table 6 illustrates the mass change, i.e. the water absorption or loss as a function of relative humidity at 25° C. for a sample of 9.5 mg of the tetrahydrate of the calcium salt of valsartan and for a period of 4 hours. The following cycles of changes in relative humidity are shown: 40-90; 90-0; 0-90; 90-0% relative humidity:

TABLE 6

| relative humidity in % | water absorption or loss in % | relative humidity in % | water absorption or Abgabe in % |
|---|---|---|---|
| 40 | 0.04 | 10 | 0.00 |
| 50 | 0.04 | 0 | −0.01 |
| 60 | 0.03 | 10 | 0.00 |
| 70 | 0.02 | 20 | 0.00 |
| 80 | 0.02 | 30 | 0.00 |
| 90 | 0.00 | 40 | 0.00 |
| 80 | 0.02 | 50 | 0.00 |
| 70 | 0.02 | 60 | 0.01 |
| 60 | 0.02 | 70 | 0.00 |
| 50 | 0.02 | 80 | −0.01 |
| 40 | 0.02 | 90 | −0.02 |
| 30 | 0.01 | 0 | −0.02 |
| 20 | 0.01 | (starting value) | 0.00 |

The measurement error of this sorption method based on thermogravimetry is about 0.1%. Therefore, the tetrahydrate of the calcium salt of valsartan under the conditions employed, which are realistic from a pharmaceutical-galenic point of view, shows no measurable water absorption or loss. This is surprising to a large extent, since the tetrahydrate, which has incorporated about 13% of bound water in the crystal structure, is totally indifferent to water even at extreme values of relative humidity. This property is crucial in the final stages of chemical manufacture and also in practice in all galenic process stages of the different dosage forms. This exceptional stability similarly benefits the patients through the constant availability of the active ingredient.

The intrinsic dissolving rates of the calcium salt of valsartan at pH 1, pH 4.5 and pH 6.8 show improved values over those of valsartan.

The exceptional stability of the calcium salt of valsartan, especially the tetrahydrate thereof, towards water may also be shown in stability tests. In these, the water content of the tetrahydrate of the calcium salt of valsartan remains constant both in an open container and in a sealed ampoule after four weeks at 40° C. and 75% relative humidity.

Owing to the advantageous crystallinity of the calcium salt, especially the tetrahydrate thereof, this salt is suitable for pressing directly to form corresponding tablet formulations.

In addition, an improved dissolving profile in a tablet can be assured. In studies of the dissolving profile, it was established that the calcium salt, especially the tetrahydrate thereof, is released by 100% from a film-coated tablet within 15 minutes.

Of the group of new-type crystalline solids, a magnesium salt hydrate of valsartan is preferred, in particular the hexahydrate. The thermal behaviour of this salt hydrate in the region of the melting point shows a certain chemical and physical instability. The thermal data are thus dependent on the measurement conditions. In the sealed gold specimen container with an internal free volume of ca. 22 microliters, with a sample of 2 to 4 mg and with a heating rate of $T_r=10$ K·min$^{-1}$, the melting point of the hexahydrate of the magnesium salt of valsarten is 132±1.5° Celsius and the melting enthalpy is 56±3 kJ·Mol$^{-1}$. The melting enthalpy which is about 5 times higher than the free acid of valsartan, together with the significantly higher melting point of the hexahydrate of the magnesium salt of valsartan is a measure of the stability of the new-type crystal grating at around room temperature.

The optical rotation of the hexahydrate of the magnesium salt of valsartan in methanol as a 1% solution at 20° C. is $[\alpha]^{20}_D = -14°$.

A measurement of the infrared absorption spectrum of the hexahydrate of the magnesium salt of valsartan in a potassium bromide compressed tablet shows the following significant bands expressed in reciprocal wave numbers (cm$^{-1}$): 3800-3000 (st); 3000-2500 (st); 1800-1500 (st); 1500-1440 (m); 1440-1300 (m); 1280-1240 (w); 1240-1190 (w); 1190-1150 (w); 1120-1070 (w); 1050-990 (w); 990-960 (w); 960-920 (w); 920-700 (m); 700-590 (w); 590-550 (w).

The intensities of the absorption bands are indicated as follows: (w)=weak; (m)=medium; and (st)=strong intensity.

Measurement of the infrared spectrum likewise took place by means of ATR-IR (Attenuated Total Reflection-Infrared Spectroscopy) using the instrument Spektrum BX from Perkin-Elmer Corp., Beaconsfield, Bucks, England.

The hexahydrate of the magnesium salt of valsartan has the following absorption bands expressed in reciprocal wave numbers (cm$^{-1}$):
3378 (m); 3274 (m); 2956 (m); 2871 (w); 2357 (w); 1684 (w); 1619 (st); 1557 (m); 1464 (m); 1419 (m); 1394 (st); 1374 (m); 1339 (w); 1319 (w); 1300 (w); 1288 (w); 1271 (w) 1255 (w); 1223 (w); 1210 (w); 1175 (m); 1140 (w); 1106 (w); 1047 (w); 1024 (w); 1015 (w); 1005 (w); 989 (w); 975 (w); 955 (w); 941 (w); 888 (w); 856 (w); 836 (m); 820 (w); 766 (st); 751 (m); 741 (st); 732 (st).

The intensities of the absorption bands are indicated as follows: (w)=weak; (m)=medium and (st)=strong intensity.

The most intensive absorption bands of the ATR-IR spectroscopy are shown by the following values expressed in reciprocal wave numbers (cm$^{-1}$): 3378 (m); 3274 (m); 2956 (m); 1619 (st); 1557 (m); 1464 (m); 1419 (m); 1394 (st); 1271 (w); 1175 (m); 1015 (w); 975 (w); 836 (m); 766 (st); 751 (m); 741 (st); 732 (st).

The error margin for all absorption bands of ATR-IR is ±2 cm$^{-1}$.

The theoretical water content of the hexahydrate of the magnesium salt of valsartan is 19.1%. Using a coupled instrument based on thermogravimetry-Fourier transformation-infrared-spectroscopy (TG-FTIR, IFS 28 from the companies Netzsch Gerätebau GmbH, Selb, Bayern and Bruker Optik GmbH, Karlsruhe), whilst simultaneously measuring the weight loss and identifying the material component given up, using infrared spectroscopy (release of water), the water content was determined at 18.5%, conforming well with the theoretical value. For the hexahydrate, this corresponds to a molar ratio of 5.8±0.2 mols H$_2$0 per mol magnesium salt.

Table 7 illustrates the water loss of the hexahydrate of the magnesium salt of valsartan depending on temperature, using the weight loss measured in an N$_2$ atmosphere on a thermogravimetric thermal analysis instrument for a heating rate of 10 K° min$^{-1}$. From the TG-FTIR measurement, the correlation of the weight loss is assured solely by the release of water.

TABLE 7

| temperature [° C.] | weight loss or water release in % |
| --- | --- |
| 25 | 0 |
| 50 | 1.2 |
| 75 | 4.2 |
| 100 | 11.0 |
| 125 | 16.7 |
| 150 | 17.7 |
| 175 | 18.3 |
| 200 | 18.5 |
| 225 | 18.7 |
| 250 | 18.9 |
| 275 | 19.3 |

The hexahydrate of the magnesium salt of valsartan has a solubility in distilled water at 22° C. of 59 g per liter of solution for a pH value of 9.3.

The crystalline form of the hexahydrate of the magnesium salt of valsartan is clearly characterised by the interlattice plane intervals calculated from the lines in an X-ray powder pattern. The measurement and analysis methods used are the same as those used for the tetrahydrate of the calcium salt of valsartan.

This preferred characterisation of the hexahydrate of the magnesium salt of valsartan is obtained from the interlattice plane intervals d, whereby, in the following, average values are indicated with the appropriate error limits:

d in [Å]: 19.7±0.3, 10.1±0.2, 9.8±0.2, 7.28±0.1, 6.48±0.1, 6.00±0.1, 5.81±0.1, 5.68±0.1, 5.40±0.05, 5.22±0.05, 5.12±0.05, 5.03±0.05, 4.88±0.05, 4.33±0.05, 4.22±0.05, 4.18±0.05, 4.08±0.05, 3.95±0.05, 3.46±0.05, 3.42±0.05.

The most intensive reflections in the X-ray diffraction diagram show the following interlattice plane intervals:

d in [Å]: 19.7±0.3, 10.11±0.2, 9.8±0.2, 7.28±0.1, 5.81±0.05, 5.68±0.05, 5.03±0.05, 4.88±0.05, 4.18±0.05, 4.08±0.05, 3.46±0.05.

A preferred method of checking the above-indicated average values of the interlattice plane intervals and intensities measured by experimentation from X-ray diffraction diagrams with a Guinier camera, for a given substance, consists in calculating these intervals and their intensities from the comprehensive single crystal structure determination. This structure determination yields cell constants and atom positions, which enable the X-ray diffraction diagram corresponding to the solid to be calculated by means of computer-aided calculation methods (programme CaRine Crystallography, Université de Compiègne, France). A comparison of these data, namely the interlattice plane intervals and intensities of the most important lines of the hexahydrate of the magnesium salt of valsartan, obtained from measurements with the Guinier camera and from calculating the single crystal data, is illustrated in Table 8.

TABLE 8

| measured | | calculated | |
| --- | --- | --- | --- |
| d in [Å] | Intensity | d in [Å] | Intensity |
| 19.7 | very strong | 19.66 | very strong |
| 10.11 | average | 10.09 | average |
| 9.83 | average | 9.84 | very strong |
| 7.28 | average | 7.27 | average |
| 6.48 | weak | 6.46 | weak |
| 6.00 | weak | 6.00 | weak |
| 5.81 | average | 5.805 | average |
| 5.68 | average | 5.676 | strong |
| 5.40 | very weak | 5.391 | very weak |
| 5.22 | weak | 5.217 | weak |
| 5.12 | weak | 5.124 | weak |
| 5.03 | strong | 5.032 | very strong |
| 4.88 | strong | 4.878 | very strong |
| 4.33 | very weak | 4.341 | weak |
| 4.22 | weak | 4.215 | weak |
| 4.18 | average | 4.181 | average |
| 4.08 | average | 4.079 | average |
| 3.95 | weak | 3.946 | weak |
| 3.46 | average | 3.463 | average |
| 3.42 | weak | 3.428 | weak |

The invention relates in particular to the crystalline hexahydrate of the magnesium salt of (S)—N-(1-carboxy-2-methylprop-1-yl)-N-pentanoyl-N-[2'-(1H-tetrazol-5-yl)biphenyl-4-ylmethyl]-amine, a crystalline solid which is clearly characterised by the data and parameters obtained from single crystal X-ray analysis. An in-depth discussion of the theory of the methods of single crystal X-ray diffraction and the definition of the evaluated crystal data and the parameters may be found in Stout & Jensen, X-Ray Structure Determination; A Practical Guide, Mac Millian Co., New York, N.Y. (1968) chapter 3.

The data and parameters of the single crystal X-ray analysis for the magnesium-valsartan-hexahydrate are given in Table 9.

TABLE 9

Crystal data and parameters of the hexahydrate of the magnesium salt of valsartan

| Crystal data | |
| --- | --- |
| sum formula | $(C_{24}H_{27}N_5O_3)^{2-}Mg^{2+} \cdot 6\ H_2O$ |
| molecular mass | 565.91 |
| crystal colour | colourless |
| crystal shape | flat prisms |
| crystal system | monoclinic |

TABLE 9-continued

Crystal data and parameters of the hexahydrate
of the magnesium salt of valsartan

| | |
|---|---|
| space group | C2 |
| size of the single crystal | 0.013 · 0.50 · 0.108 mm³ |
| dimensions and angle of elementary cell | a = 40.075(8) Å |
| | b = 7.400(1) Å |
| | c = 10.275(2) Å |
| | α = 90° |
| | β = 100.85(3)° |
| | γ = 90° |
| volume of elementary cell | $V_c$ = 2992.6(9) Å³ |
| number of molecules in the elementary cell | 4 |
| F (000) | 1208 |
| measurement range of cell parameters (Θ) | 2.82-11.15° |
| calculated density | 1.256 (g · cm⁻³) |
| linear absorption coefficient | 0.114 mm⁻¹ |
| X-ray measurement data | |
| diffractometer | Enraf Nonius CAD4 |
| X-radiation (graphite monochromator) | MoKα |
| wavelength | 0.71073 |
| temperature | 295 K |
| scan range (θ) | 1.03-26.00° |
| scan mode | ω/2 Θ |
| reflections collected/unique | 5954/5868 |
| number of significant reflections (I > 2σ(I)) | 1341 |
| variation in intensity | <1% |
| absorption correction | numeric |
| Structure refinement | |
| method | full matrix, least squares, F² |
| number of parameters | 243 |
| agreement index (R) | 10.7% |
| weighted agreement index ($R_W$) | 13.8% |
| S factor (Goodness of fit) | 1.001 |
| number of reflections used | 5868 |
| determination of hydrogen atoms | majority according to the "riding" model, nine H-atoms from water molecules isotropically refined from difference-Fourier calculation |
| extinction correction | 0.00098 (10) |
| maximum/minimum residual electron density in final difference-Fourier calculation | 0.473/−0.614 (e · Å⁻³) |
| absolute structure parameters | 0.0(10) |

Computer programmes used
SHELXS 86 (Sheldrick, Göttingen, 1990)
SHELXL 96 (Sheldrick, Göttingen, 1996)
SCHAKAL 86 (Keller, Freiburg 1986)
PLATON (Spek, Acta Cryst., 1990)

The elementary cell is defined by six parameters, namely by the grating constants a, b and c, and by the axial angle, namely by α, β, and γ. In this way, the volume of the elementary cell $V_c$ is determined. A differentiated description of these crystal parameters is illustrated in chapter 3 of Stout & Jensen (see above).

The details for the hexahydrate of the magnesium salt of valsartan from the single crystal measurements, especially the atom coordinates, the isotropic thermal parameters, the coordinates of the hydrogen atoms as well as the corresponding isotropic thermal parameters, show that a monoclinic elementary cell exists, its cell content occurring from four formula units $Mg^{2+}$ Valsartan.$6H_2O$.

Given the acentric space group C2 determined from the single crystal X-ray structure determination, a racemate is ruled out. Thus the enantiomeric purity of the S-configuration for the crystalline hexahydrate of the magnesium salt of valsartan is proved.

Table 10 illustrates the mass change, i.e. the water absorption or loss as a function of relative humidity at 25° C. for a sample of 9.5 mg of magnesium-valsartan-hexahydrate and for a period of 4 hours (h). The following cycles of changes in relative humidity are shown: 40-90; 90-0; 0-90; 90-0% relative humidity:

TABLE 10

| relative humidity in % | water absorption or loss in % | relative humidity in % | water absorption or loss in % |
|---|---|---|---|
| 40 | 0.06 | 10 | −0.12 |
| 50 | 0.14 | 0 | −4.3 |
| 60 | 0.19 | 10 | −0.79 |
| 70 | 0.25 | 20 | −0.14 |
| 80 | 0.41 | 30 | −0.05 |
| 90 | 0.58 | 40 | 0.02 |
| 80 | 0.32 | 50 | 0.09 |
| 70 | 0.22 | 60 | 0.14 |
| 60 | 0.14 | 70 | 0.20 |
| 50 | 0.08 | 80 | 0.28 |
| 40 | 0.16 | 90 | 0.51 |
| 30 | −0.03 | 0 | −3.68 |
| 20 | −0.07 | (starting value) | −0.01 |

The measurement error of this sorption method based on thermogravimetry is about 0.1%. Therefore, the hexahydrate of the magnesium salt of valsartan under the conditions employed, which are realistic from a pharmaceutical-galenic point of view, shows weak, reproducible water absorption or water loss in a range of 20 to 80% relative humidity. This is surprising to a large extent, since the hexahydrate, which has incorporated about 19% bound water in the crystal structure, reversibly absorbs or releases water even at extreme values of relative humidity and is relatively insensitive at an average range of relative humidity. This characteristic enables an uncomplicated physical-chemical process to be developed and allows a choice of the best dosage forms for the patients.

The exceptional stability of the magnesium salt of valsartan, especially the hexahydrate thereof, towards water may also be shown in stability tests In these, the water content of the hexahydrate of the magnesium salt of valsartan remains constant both in an open container and in a sealed ampoule after four weeks at 40° C. and 75% relative humidity.

Owing to the advantageous crystallinity of the magnesium salt, especially the hexahydrate thereof, this salt is suitable for pressing directly to form corresponding tablet formulations.

In addition, an improved dissolving profile in a tablet can be assured. In studies of the dissolving profile, it was established that the magnesium salt, especially the hexahydrate thereof, is released by 100% from a film-coated tablet within 15 minutes.

In addition, the magnesium salt of valsartan, especially the hexahydrate thereof, shows an advantageous compression hardness profile.

Calcium/magnesium mixed salts of valsartan also have advantageous properties, for example uniform crystal conglomerates may be produced. These may be advantageously used in the galenic formulation.

The intrinsic dissolving rates of the di-potassium salt of valsartan at pH 1, pH 4.5 and pH 6.8 show improved values over those of valsartan.

A further object of the invention is the preparation of the salts according to the invention.

The salts according to the invention, including amorphous or crystalline forms thereof, may be prepared as follows:

To form the salt, the process is carried out in a solvent system, in which the two reactants, namely the acid valsartan and the respective base, are sufficiently soluble. It is expedient to use a solvent or solvent mixture, in which the resulting salt is only slightly soluble or not soluble at all, in order to achieve crystallisation or precipitation. One variant for the salt according to the invention would be to use a solvent in which this salt is very soluble, and to subsequently add an anti-solvent to this solution, that is a solvent in which the resulting salt has only poor solubility. A further variant for salt crystallisation consists in concentrating the salt solution, for example by heating, if necessary under reduced pressure, or by slowly evaporating the solvent, e.g. at room temperature, or by seeding with the addition of seeding crystals, or by setting up water activity required for hydrate formation.

The solvents that may be used are for example $C_1$-$C_5$-alkanols, preferably ethanol and isopropanol, as well as $C_1$-$C_5$-dialkylketones, preferably acetone and mixtures thereof with water.

The antisolvents for salt crystallisation may be for example $C_3$-$C_7$-alkylnitriles, especially acetonitrile, esters, especially $C_2$-$C_7$-alkanecarboxylic acid-$C_1$-$C_5$-alkylester, such as ethyl or isopropyl acetate, di-($C_1$-$C_5$-alkyl)-ethers, such as tert.-butylmethylether, furthermore tetrahydrofuran, and $C_5$-$C_8$-alkanes, especially pentane, hexane or heptane.

To produce hydrates, a dissolving and crystallising process is used in particular, or a water-equilibrating crystallisation process.

The dissolving and crystallising process is characterised in that
(i) valsartan and the appropriate base are brought to a reaction in a preferably water-containing, organic solvent,
(ii) the solvent system is concentrated, for example by heating, if necessary under reduced pressure and by seeding with seeding crystals or by slowly evaporating, e.g. at room temperature, then crystallisation or precipitation is initiated and
(iii) the salt obtained is isolated.

In the dissolving and crystallising process, the water-containing, organic solvent system employed is advantageously a mixtures of alcohols, such as ethanol, and water, or or alkyl-nitrile, especially acetonitrile, and water.

The equilibrating crystallisation process for producing hydrates is characterised in that
(i) valsartan and the appropriate base are added to a water-containing organic solvent,
(ii) the solvent is concentrated, for example by heating, if necessary under reduced pressure or by slowly evaporating, e.g. at room temperature,
(iii) the residue of evaporation is equilibrated with the required amount of water by
(a) suspending the residue of evaporation, which is advantageously still warm, and which still contains some water, in an appropriate solvent or
(b) by equilibrating the water excess in the solvent;
whereby in a) and b) the existing or added water is present in a quantity in which the water dissolves in the organic solvent and does not form an additional phase; and
(iv) the salt obtained is isolated.

The solvent system used as the water-containing organic solvent advantageously comprises mixtures of suitable alcohols, such as $C_1$-$C_7$-alkanols, especially ethanol, and water.

An appropriate solvent for equilibration is, for example, an ester such as $C_1$-$C_7$-alkanecarboxylic acid-$C_1$-$C_7$-alkylester, especially ethyl acetate, or a ketone such as di-$C_1$-$C_5$-alkylketone, especially acetone.

The equilibration process is notable for example for its high yields and outstanding reproducibility.

When producing the mono-alkali metal salts according to the present invention, predominantly amorphous forms are obtained. On the other hand, the di-alkali metal salts and alkaline earth metal salts of the present invention may also be obtained in crystalline form and are in the form of hydrates throughout, from appropriate solvents that are conventionally used in production processes, such as esters, e.g. $C_1$-$C_7$-alkanecarboxylic acid-$C_1$-$C_7$-alkylesters, especially ethyl acetate, ketones, e.g. di-$C_1$-$C_5$-alkylketones, especially acetone, $C_3$-$C_7$-alkylnitriles, especially acetonitrile, or ethers, e.g. di-($C_1$-$C_5$-alkyl)-ethers, such as tert.-butylmethylether, also tetrahydrofuran, or mixtures of solvents. By using the dissolving and crystallising process, or the water-equilibrating crystallisation process, the defined hydrates, which are present in crystalline and in polymorphous forms, may be obtained reproducibly.

The preparation of the hydrate-free bis-dialkylammonium salts of the present invention is advantageously effected in one step by using an appropriate solvent which is optionally mixed with an antisolvent. In this way, crystalline salts are obtained.

As a rule, the amino acid salts of the present invention are obtained in amorphous form.

The processes for forming salts are likewise objects of the present invention.

These salts or salt hydrates according to the invention are obtained for example by neutralising the acid valsartan with a base corresponding to the respective cation. This neutralisation is suitably effected in an aqueous medium, e.g. in water or a mixture of water and a solvent in which valsartan is more soluble than in water. Salts with weaker bases may be converted into other salts either by treating with stronger bases or by treating with acids and then neutralising with other bases.

Crystallisation, especially of the alkaline earth salt hydrates, is effected in water or an aqueous medium, which consists of water and at least one solvent that is miscible or partially miscible with water, i.e. not too non-polar, e.g. an alkanol such as methanol, ethanol, propanol, isopropanol, butanol, acetone, methyl ethyl ketone, acetonitrile, DMF, DMSO. The alkanol portion amounts to about 10 to 90, or 20 to 70, advantageously 30 to 50% by volume. For higher alkanols, the less polar solvent may also be present in lower concentrations. Owing to the restricted water-solubility of valsartan, the process frequently takes place in suspensions, or if valsartan is soluble in the other solvent component, in a solution.

In one embodiment, for example to produce the calcium salt of valsartan, an aqueous solution of valsartan is neutralised with a calcium hydroxide solution at room temperature and the solution is left to crystallise. In a preferred procedure, crystallisation is effected from a solvent mixture of water/ethanol, the ethanol proportion amounting to ca. 30 to 50% by volume. In an especially preferred form, crystallisation is effected in a closed system by transporting through a low temperature gradient (especially 1-2° C. at 40° C.) in 30% by volume of ethanol.

In a preferred variant, crystallisation may be optimised, e.g. accelerated, by adding at least one seed crystal.

The salts according to the invention may be used e.g. in the form of pharmaceutical preparations, which contain the active substance e.g. in a therapeutically effective amount of the active substance, optionally together with a pharmaceutically acceptable carrier, for example with an inorganic or organic, solid or optionally also liquid pharmaceutically acceptable carrier, which is suitable for enteral, e.g. oral, or parenteral administration.

The invention relates in particular to a pharmaceutical composition, especially in a solid dosage unit, preferably for oral administration, optionally together with a pharmaceutically acceptable carrier.

Pharmaceutical preparations of this kind may be used for example for the prophylaxis and treatment of diseases or conditions which may be inhibited by blocking the $AT_1$ receptor for example a disease or condition selected from the group consisting of
(a) hypertension, congestive heart failure, renal failure, especially chronic renal failure, restenosis after percutaneous transluminal angioplasty, and restenosis after coronary artery bypass surgery;
(b) atherosclerosis, insulin resistance and syndrome X, diabetes mellitus type 2, obesity, nephropathy, renal failure, e.g. chronic renal failure, hypothyroidism, survival post myocardial infarction (MI), coronary heart diseases, hypertension in the elderly, familial dyslipidemic hypertension, increase of formation of collagen, fibrosis, and remodeling following hypertension (antiproliferative effect of the combination), all these diseases or conditions associated with or without hypertension;
(c) endothelial dysfunction with or without hypertension,
(d) hyperlipidemia, hyperlipoproteinemia, atherosclerosis and hypercholesterolemia, and
(e) glaucoma.

Primary usages are for the treatment of high blood pressure and congestive heart failure, as well as post-myocardial infarction.

The person skilled in the pertinent art is fully enabled to select a relevant and standard animal test model to prove the hereinbefore and hereinafter indicated therapeutic indications and beneficial effects.

The pharmaceutical activities as effected by administration of representatives of the salts of the present invention or of the combination of active agents used according to the present invention can be demonstrated e.g. by using corresponding pharmacological models known in the pertinent art. The person skilled in the pertinent art is fully enabled to select a relevant animal test model to prove the hereinbefore and hereinafter indicated therapeutic indications and beneficial effects.

These beneficial effects can, for example, be demonstrated in the test model as disclosed by G. Jeremic et al. in J. Cardovasc. Pharmacol. 27:347-354, 1996.

For example, the valuable potential of the salts or combinations of the present invention for the prevention and treatment of myocardial infarction can be found using the following test model.

Study Design

In the study to be performed, permanent coronary artery occlusion (CAO) in rats is used as a model of acute myocardial infarction. The experiments are carried out with 5 treatment groups characterized by following features:
sham-operated animals
CAO+vehicle
CAO+a salt according to the present invention, optionally
CAO+a salt according to the present invention+a combination partner.

During the study following variables are measured:
infarct size
LV chamber volume
interstitial and perivascular collagen density in spared LV myocardium
COL-I and COL-III protein content in spared LV myocardium by Western blot
cardiomyocytes cross-sectional area and length in sections of LV myocardium
plasma concentrations of renin and aldosterone
urine concentration of sodium, potassium and aldosterone
blood pressure in conscious animals
LV and carotid blood pressure in anesthetized animals.

Methodology

Infarct Size:

Six μm-thick transverse histological sections of the left ventricle are stained with nitroblue tetrazolium and acquired by a B/W XC-77CE CCD video camera (Sony). The resulting image is processed on a KS 300 image analysis system (Carl Zeiss Vision) using a software specifically developed (Porzio et al., 1995). A single operator blinded to treatment interactively defines the boundaries of the interventricular septum, and the infarcted area on each section is semiautomatically identified as the area of unstained ventricular tissue. The software automatically calculates for each component of the ventricular section defined as the chamber, septum, infarcted area, infarcted LV wall and viable LV wall, a set of geometric parameters (Porzio et al., 1995).

Histology:

Hearts are fixed in situ, by retrograde perfusion with buffered 4% formaldehyde after arrest in diastole by i.v. injection of 0.5 M KCl. After fixation, the left ventricle (LV) and the free wall of the right ventricle are separately weighed; LV longer diameter is measured with a caliper. LV histological sections are stained with hematoxylin & eosin for qualitative examination and to quantify cardiomyocytes cross-sectional area with a semi-automated image analysis routine. Interstitial collagen deposition in LV is evaluated on Sirius red stained sections with a semi-automated image analysis routine (Masson et al., 1998).

Collagen Content in LV Spared Myocardium:

LV tissue in the spared myocardium is homogenized, subjected to PAGE-SDS electrophoresis and electroblotted onto nitrocellulose membrane. The blots are exposed to primary antibodies, i.e. rabbit anti-rat collagen type I or type III antiserum (Chemicon). The primary antibodies are recognized by secondary antibodies conjugated to alkaline phosphatase (for colagen type I) or peroxidase (collagen type III).

Left Ventricular Chamber Volume:

LV chamber volume is determined in hearts arrested in diastole (KCl) and fixed in formalin under a hydrostatic pressure equivalent to the measured LV end-diastolic pressure. A metric rod is inserted into the LV to measure LV inner length. The transverse diameters of the LV chamber are measured in two 1-mm thick transverse sections near to the base and the apex of the ventricle (Jeremic et al., 1996). The chamber volume is computed from an equation integrating transverse diameters and inner length.

Systemic and Left Ventricular Hemodynamics:

A microtip pressure transducer (Millar SPC-320) connected to a recorder (Windograf, Gould Electronics) is inserted into the right carotid artery to record systolic and diastolic blood pressures. The pressure transducer is advanced into the LV to measure LV systolic (LVSP) and end-diastolic (LVEDP) pressures, the first derivative of LV pressure over time (+dP/dt) and heart rate.

Non-Invasive Blood Pressure:

Systolic blood pressure and heart rate are measured by the tail-cuff method (Letica LE 5002) in conscious rats.

Urine Electrolytes, Hormones:

Rats are individually housed in metabolic cages and 24-h urine collected on 1 ml HCl 6N. Water intake is measured. Urine catecholamines are extracted on Bondelut $C_{18}$ columns (Varian), separated by HPLC (Apex-II C18, 3 µm, 50×4.5 mm analytical column, Jones Chromatography) and quantified with an electrochemical detector (Coulochem II, ESA) (Goldstein et al., 1981). Plasma and urine aldosterone, and plasma angiotensin II is determined with specific radioimmunoassays (Aldoctk-2, DiaSorin and Angiotensin II, Nichols Diagnostics). Urine sodium and potassium are measured by flamme photometry.

Sample Size 10 animals analyzable in each treatment groups are sufficient to detect biologically significant differences. Only rats with an infarct size of at least 10% of the LV section area are included in the final analysis.

Endothelial dysfunction is being acknowledged as a critical factor in vascular diseases. The endothelium plays a bimodal role as the source of various hormones or by-products with opposing effects: vasodilation and vasoconstriction, inhibition or promotion of growth, fibrinolysis or thrombogenesis, production of anti-oxidants or oxidising agents. Genetically predisposed hypertensive animals with endothelial dysfunction constitute a valid model for assessing the efficacy of a cardiovascular therapy.

Endothelial disfunction is characterized by, for example, increased oxidative stress, causing decreased nitric oxide, increased factors involved in coagulation or fibrinolysis such as plasminogen activating inhibitor-1 (PAI-1), tissue factor (TF), tissue plasminogen activator (tPA), increased adhesion molecules such as ICAM and VCAM, increased growth factors such as bFGF, TGFb, PDGF, VEGF, all factors causing cell growth inflammation and fibrosis.

The treatment e.g. of endothelian dysfunction can be demonstrated in the following pharmacological test:

Material and Methods

Male 20-24 week-old SHR, purchased from RCC Ldt (Füllingsdorf, Switzerland), are maintained in a temperature- and light-controlled room with free access to rat chow (Nafag 9331, Gossau, Switzerland) and tap water. The experiment is performed in accordance with the NIH guidelines and approved by the Canton Veterinary office (Bew 161, Kantonales Veterinäramt, Liestal, Switzerland). All rats are treated with the NO synthesis inhibitor L-NAME (Sigma Chemicals) administered in drinking water (50 mg/l) for 12 weeks. The average daily dose of L-NAME calculated from the water consumed was 2.5 mg/kg/d (range 2.1-2.7).

The rats can be divided into 2 or 3 groups: group 1, control (n=e.g. 40); Group 2, a salt according to the present invention; n=e.g. 40); for testing combinations Group 3, combination partner; (n=e.g. 30). The drugs are administered in drinking fluid. The pressure effect of Ang II at 1 mg/kg obtained in controls normotensive rats can be reduced after treatment with a salt according to the present invention (Gervais et al. 1999).

Body weight is measured every week. Systolic blood pressure and heart rate are recorded by tail cuff plethysmography 3 and 2 weeks before starting the study and at 2 weeks after drug administration. Urine is collected over a 24 hour period from rats kept in individual (metabolic) cages the week before starting treatment and at weeks 4 and 12 for volume measurement and protein, creatinine, sodium and potassium determination using standard laboratory methods. At the same time points, blood samples are withdrawn from the retro-orbital plexus (maximum 1 ml) for creatinine, $Na^+$ and $K^+$ assays.

Ten rats from each group are sacrificed at 4 weeks for collection of kidney and heart for morphological analysis. The remaining rats are sacrificed at 12 weeks. Cardiac and kidney weight is recorded. Terminal blood sampling is performed in 5% EDTA at 4 (morphometry study) and 12 (end of the study) weeks for aldosterone, determination by radioimmunoassay using a DPC coat-a-count aldosterone-RIA kit (Bühlmann, Switzerland).

Statistical Analysis:

All data are expressed as mean±SEM. Statistical analysis is performed using a one-way ANOVA, followed by a Duncan's multiple range test and a Newman-Keuls test, 7 for comparison between the different groups. Results with a probability value of less than 0.05 are deemed statistically significant.

An improvement of regression of artherosclerosis without effecting the serum lipid levels can, for example, be demonstrated by using the animal model as disclosed by H. Kano et al. in Biochemical and Biophysical Research Communications 259, 414-419 (1999).

That the salts or combinations according to the present invention can be used for the regression of a cholesterol diet-induced atherosclerosis, can be demonstrated using the test model described, e.g., by C. Jiang et al. in Br. J. Pharmacol. (1991), 104, 1033-1037.

That the salts or combinations according to the present invention can be used for the treatment of renal failure, especially chronic renal failure, can be demonstrated using the test model described, e.g., by D. Cohen et al. in Journal of Cardiovascular Pharmacology, 32: 87-95 (1998).

The present pharmaceutical preparations which, if so desired, may contain further pharmacologically active substances, are prepared in a manner known per se, for example by means of conventional mixing, granulating, coating, dissolving or lyophilising processes, and contain from about 0.1% to 100%, especially from about 1% to about 50%, of lyophilisates up to 100% of the active substance.

The invention similarly relates to compositions containing the salts according to the invention.

The invention similarly relates to the use of the salts according to the invention preferably for the production of pharmaceutical preparations, especially for the prophylaxis and also for the treatment of diseases or conditions which may be inhibited by blocking the $AT_1$ receptor.

Primary usages are for the treatment of high blood pressure and congestive heart failure, as well as post-myocardial infarction.

The invention similarly relates to the use for the prophylaxis and treatment of diseases or conditions which may be inhibited by blocking the $AT_1$ receptor, characterised in that a patient, including a human patient, requiring such treatment is administered with a therapeutically effective amount of a salt according to the invention, optionally in combination with at least one composition for the treatment of cardiovascular diseases and related conditions and diseases listed hereinbefore or hereinafter.

The invention similarly relates to combinations, e.g. pharmaceutical combinations, containing a salt of the present invention or in each case a pharmaceutically acceptable salt thereof in combination with at least one composition for the treatment of cardiovascular diseases and related conditions and diseases as listed hereinbefore or hereinafter, or in each case a pharmaceutically acceptable salt thereof. Combinations with other compositions for the treatment of cardiovascular diseases and related conditions and diseases as listed hereinbefore or hereinafter, or in each case a pharmaceutically acceptable salt thereof, are likewise objects of the present invention.

The combination may be made for example with the following compositions, selected from the group consisting of a:
(i) HMG-Co-A reductase inhibitor or a pharmaceutically acceptable salt thereof,
(ii) angiotensin converting enzyme (ACE) Inhibitor or a pharmaceutically acceptable salt thereof,
(iii) calcium channel blocker or a pharmaceutically acceptable salt thereof,
(iv) aldosterone synthase inhibitor or a pharmaceutically acceptable salt thereof,
(v) aldosterone antagonist or a pharmaceutically acceptable salt thereof,
(vi) dual angiotensin converting enzyme/neutral endopeptidase (ACE/NEP) inhibitor or a pharmaceutically acceptable salt thereof,
(vii) endothelin antagonist or a pharmaceutically acceptable salt thereof,
(viii) renin inhibitor or a pharmaceutically acceptable salt thereof, and
(ix) diuretic or a pharmaceutically acceptable salt thereof.

HMG-Co-A reductase inhibitors (also called β-hydroxy-β-methylglutaryl-co-enzyme-A reductase inhibitors) are understood to be those active agents that may be used to lower the lipid levels including cholesterol in blood.

The class of HMG-Co-A reductase inhibitors comprises compounds having differing structural features. For example, mention may be made of the compounds that are selected from the group consisting of atorvastatin, cerivastatin, compactin, dalvastatin, dihydrocompactin, fluindostatin, fluvastatin, lovastatin, pitavastatin, mevastatin, pravastatin, rivastatin, simvastatin, and velostatin, or, in each case, a pharmaceutically acceptable salt thereof.

Preferred HMG-Co-A reductase inhibitors are those agents which have been marketed, most preferred is fluvastatin and pitavastatin or, in each case, a pharmaceutically acceptable salt thereof.

The interruption of the enzymatic degradation of angiotensin I to angiotensin II with so-called ACE-inhibitors (also called angiotensin converting enzyme inhibitors) is a successful variant for the regulation of blood pressure and thus also makes available a therapeutic method for the treatment of congestive heart failure.

The class of ACE inhibitors comprises compounds having differing structural features. For example, mention may be made of the compounds which are selected from the group consisting alacepril, benazepril, benazeprilat, captopril, ceronapril, cilazapril, delapril, enalapril, enaprilat, fosinopril, imidapril, lisinopril, moveltopril, perindopril, quinapril, ramipril, spirapril, temocapril, and trandolapril, or, in each case, a pharmaceutically acceptable salt thereof.

Preferred ACE inhibitors are those agents that have been marketed, most preferred are benazepril and enalapril.

The class of CCBs essentially comprises dihydropyridines (DHPs) and non-DHPs such as diltiazem-type and verapamil-type CCBs.

A CCB useful in said combination is preferably a DHP representative selected from the group consisting of amlodipine, felodipine, ryosidine, isradipine, lacidipine, nicardipine, nifedipine, niguldipine, niludipine, nimodipine, nisoldipine, nitrendipine, and nivaldipine, and is preferably a non-DHP representative selected from the group consisting of flunarizine, prenylamine, diltiazem, fendiline, gallopamil, mibefradil, anipamil, tiapamil and verapamil, and in each case, a pharmaceutically acceptable salt thereof. All these CCBs are therapeutically used, e.g. as anti-hypertensive, anti-angina pectoris or anti-arrhythmic drugs.

Preferred CCBs comprise amlodipine, diltiazem, isradipine, nicardipine, nifedipine, nimodipine, nisoldipine, nitrendipine, and verapamil, or, e.g. dependent on the specific CCB, a pharmaceutically acceptable salt thereof. Especially preferred as DHP is amlodipine or a pharmaceutically acceptable salt, especially the besylate, thereof. An especially preferred representative of non-DHPs is verapamil or a pharmaceutically acceptable salt, especially the hydrochloride, thereof.

Aldosterone synthase inhibitor is an enzyme that converts corticosterone to aldosterone to by hydroxylating cortocosterone to form 18-OH-corticosterone and 18-OH-corticosterone to aldosterone. The class of aldosterone synthase inhibitors is known to be applied for the treatment of hypertension and primary aldosteronism comprises both steroidal and non-steroidal aldosterone synthase inhibitors, the later being most preferred.

Preference is given to commercially available aldosterone synthase inhibitors or those aldosterone synthase inhibitors that have been approved by the health authorities.

The class of aldosterone synthase inhibitors comprises compounds having differing structural features. For example, mention may be made of the compounds which are selected from the group consisting of the non-steroidal aromatase inhibitors anastrozole, fadrozole (including the (+)-enantiomer thereof), as well as the steroidal aromatase inhibitor exemestane, or, in each case where applicable, a pharmaceutically acceptable salt thereof.

The most preferred non-steroidal aldosterone synthase inhibitor is the (+)-enantiomer of the hydrochloride of fadrozole (U.S. Pat. Nos. 4,617,307 and 4,889,861) of formula

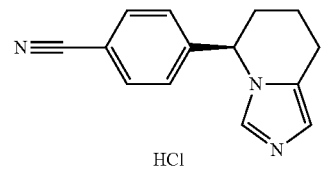

A preferred steroidal aldosterone antagonist is eplerenone of the formula

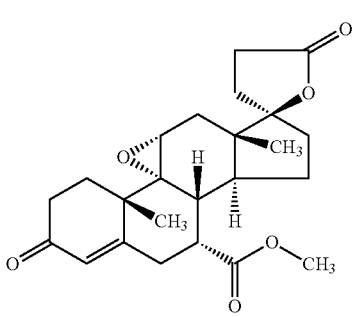

or spironolactone.

A preferred dual angiotensin converting enzyme/neutral endopetidase (ACE/NEP) inhibitor is, for example, omapatrilate (cf. EP 629627), fasidotril or fasidotrilate, or, if appropriable, a pharmaceutically acceptable salt thereof.

A preferred endothelin antagonist is, for example, bosentan (cf. EP 526708 A), furthermore, tezosentan (cf. WO 96/19459), or in each case, a pharmaceutically acceptable salt thereof.

A renin inhibitor is, for example, a non-peptidic renin inhibitor such as the compound of formula

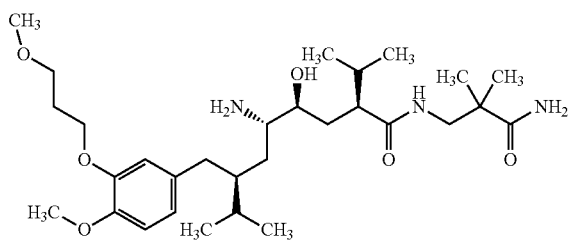 [SMILES: COCCCOc1cc(C[C@@H](C[C@H](N)[C@@H](O)C[C@H](C(=O)NCC(C)(C)C(N)=O)C(C)C)C(C)C)ccc1OC]

chemically defined as 2(S),4(S),5(S),7(S)—N-(3-amino-2,2-dimethyl-3-oxopropyl)-2,7-di(1-methylethyl)-4-hydroxy-5-amino-8-[4-methoxy-3-(3-methoxy-propoxy)phenyl]octanamide. This representative is specifically disclosed in EP 678503A. Especially preferred is the hemi-fumarate salt thereof.

A diuretic is, for example, a thiazide derivative selected from the group consisting of chlorothiazide, hydrochlorothiazide, methylclothiazide, and chlorothalidon. The most preferred is hydrochlorothiazide.

Preferably, the jointly therapeutically effective amounts of the active agents according to the combination of the present invention can be administered simultaneously or sequentially in any order, separately or in a fixed combination.

The structure of the active agents identified by generic or tradenames may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active agents and, based on these references, likewise enabled to manufacture and test the pharmaceutical indications and properties in standard test models, both in vitro and in vivo.

The corresponding active ingredients or a pharmaceutically acceptable salts thereof may also be used in form of a solvate, such as a hydrate or including other solvents, used for crystallization.

The compounds to be combined can be present as pharmaceutically acceptable salts. If these compounds have, for example, at least one basic center, they can form acid addition salts. Corresponding acid addition salts can also be formed having, if desired, an additionally present basic center. The compounds having an acid group (for example COOH) can also form salts with bases.

In a variation thereof, the present invention likewise relates to a "kit-of-parts", for example, in the sense that the components to be combined according to the present invention can be dosed independently or by use of different fixed combinations with distinguished amounts of the components, i.e. simultaneously or at different time points. The parts of the kit of parts can then e.g. be administered simultaneously or chronologically staggered, that is at different time points and with equal or different time intervals for any part of the kit of parts. Preferably, the time intervals are chosen such that the effect on the treated disease or condition in the combined use of the parts is larger than the effect that would be obtained by use of only any one of the components.

The invention furthermore relates to a commercial package comprising the combination according to the present invention together with instructions for simultaneous, separate or sequential use.

Dosaging may depend on various factors, such as mode of application, species, age and/or individual condition. For oral application, the doses to be administered daily are between ca. 0.25 and 10 mg/kg, and for warm-blooded animals with a body weight of ca. 70 kg, preferably between ca. 20 mg and 500 mg, especially 40 mg, 80 mg, 160 mg and 320 mg based on the free acid.

The invention is illustrated in particular by the examples and also relates to the new compounds named in the examples and to their usage and to methods for the preparation thereof.

The following examples serve to illustrate the invention without limiting the invention in any way.

For example, the di-potassium salt of valsartan is formed, especially a hydrate thereof. The di-potassium salt is noted in particular for its marked water solubility. The crystalline tetrahydrate of the di-potassium salt of valsartan, with a melting point of 135.0° C., may be mentioned in particular. According to elementary analysis, a certain sample of this hydrate has a water content of 3.72 mols of water per mol of di-potassium salt. For high relative humidity at room temperature, the tetrahydrate is formed and for low values of relative humidity, the anhydrate of the di-potassium salt is formed.

A magnesium salt of valsartan is similarly produced, in this instance as an amorphous solid with 3.4% $H_2O$. The temperature of glass transition, as a mean value of the stage of the specific heat of 0.85 $J \cdot [g \cdot ° C.]^{-1}$ is 167° C. No melting point is observed. Both facts, namely the glass transition and the absence of a melting point, together with the measured value of the change in specific heat, confirm that this magnesium salt of valsartan is practically 100% amorphous. According to a stereo-specific chromatography method, the enantiomer purity of this amorphous magnesium salt has been determined as 83%.

EXAMPLE 1

Production of the calcium salt as the tetrahydrate in situ of (S)—N-(1-carboxy-2-methyl-prop-1-yl)-N-pentanoyl-N-[2'-(1H-tetrazol-5-yl)-biphenyl-4-ylmethyl]-amine 21.775 g of (S)—N-(1-carboxy-2-methyl-prop-1-yl)-N-pentanoyl-N-[2'-(1H-tetrazol-5-yl)-biphenyl-4-ylmethyl]-amine are dissolved at room temperature in 300 ml of ethanol. By careful addition of 300 ml of water, the ethanol concentration is reduced to 50% by volume. Using a magnetic stirrer, 3.89 g of $Ca(OH)_2$ are added slowly in small portions to this clear, slightly acidic (pH 4) solution, so that the pH value temporarily does not exceed a value of ca. 8. Because it absorbs $CO_2$ from the air, the $Ca(OH)_2$ used contains traces of $CaCO_3$; therefore the added amount includes an excess of 5%. After adding the stoichiometric amount of $Ca(OH)_2$, the pH is ca. 6, and after adding the excess it rises to 7. The solution becomes turbid through the small amount of finely divided $CaCO_3$, which is removed through a folded filter. The product contained in the solution crystallises continuously upon removal of the alcohol content by allowing to stand at room temperature. The procedure can be accelerated by using a flat dish in a recirculating air drier at 40° C. After concentrating to ca. one half, the alcohol content of the solution drops to ca. 10% by volume and most of the product crystallises. It is filtered, rinsed for a short time with 10% by volume ethanol and dried at 40° C. until reaching a constant weight. (S)—N-(1-carboxy-2-methyl-prop-1-yl)-N-pentanoyl-N-[2'-(1H-tetrazol-5-yl)-biphenyl-4-ylmethyl]-amine calcium salt tetrahydrate is obtained.

The melting point for the tetrahydrate of the calcium salt of valsartan, produced according to example 1, for a heating rate of 10 K·min$^{-1}$ and in a closed specimen container with a small internal volume is determined as 205° C. and the melting enthalpy as 92 K·Mol$^{-1}$.

The density of the crystals of the calcium-valsartan-tetrahydrate produced according to example 1, determined by a helium pycnometer, is 1.297 g·cm$^{-3}$. This value conforms to the theoretically calculated value of 1.298 g·cm$^{-3}$ calculated from the single crystal structure. The optical rotation of the tetrahydrate of the calcium salt of valsartan according to example 1 is measured in methanol as a 1% solution $[\alpha]^{20}_D = +1°$.

The enantiomer purity of the salt hydrate produced according to example 1 is determined by a stereo-specific HPLC method. The stereo-specific separation is achieved by a chiral column (Chiral AGP). The enantiomer purity is determined as ee=100%.

Calculation of the interlattice plane intervals from the X-ray powder pattern taken with a Guinier camera is as follows for the most important lines for this batch of the tetrahydrate of the calcium salt of valsartan:

d in [Å]: 16.27, 9.90, 9.39, 8.04, 7.71, 7.05, 6.49, 6.34, 6.2, 5.87, 5.75, 5.66, 5.20, 5.05, 4.95, 4.73, 4.55, 4.33, 4.15, 4.12, 3.95, 3.91, 3.87, 3.35.

Elementary analysis gives the following measured values of the elements present in calcium-valsartan-tetrahydrate and of water. The water evaluation was carried out at 130° C. after expulsion. The findings of the elementary analysis, within the error limits, correspond to the sum formula $(C_{24}H_{27}N_5O_3)^{2-}Ca^{2+}\cdot 4H_2O$.

|  | % found | % calculated |
| --- | --- | --- |
| C | 52.82 | 52.83 |
| H | 6.42 | 6.47 |
| N | 12.91 | 12.83 |
| O | 20.20 | 20.53 |
| water | 13.25 | 13.21 |
| Ca | 7.03 | 7.35 |

EXAMPLE 2

Production of the magnesium salt as the hexahydrate in situ of (S)—N-(1-carboxy-2-methyl-prop-1-yl)-N-pentanoyl-N-[2'-(1H-tetrazol-5-yl)-biphenyl-4-ylmethyl]-amine 43.55 g of valsartan [(S)—N-(1-carboxy-2-methyl-prop-1-yl)-N-pentanoyl-N-[2'-(1H-tetrazol-5-yl)-biphenyl-4-ylmethyl]-amine] are dissolved at room temperature in 600 ml of 50% by volume ethanol (from absolute ethanol—see Merck and quarz-bidistilled water). The slightly turbid solution becomes clear after adding a further 50 ml of 50% ethanol. Using a magnetic stirrer, 4.03 g or 0.1 M MgO (Merck p.a.) are slowly added in small portions to this slightly acidic solution with a pH value of 4. The pH value hereby rises to ca. 6. The process is effected with an excess of 10%, i.e. a further 0.40 g of MgO are added. This excess is not fully dissolved, and the pH value rises to ca. 7.5. The small residue is filtered from the solution through a folded filter and washed with 50 ml of 50% ethanol.

The combined clear solution is carefully concentrated at 40° C. whilst stirring with a magnetic stirrer in a large crystallisation dish. Towards the end of this procedure, the solution has a tendency to harden into a glassy gel. Scratching with a glass rod induces the in situ crystallisation in this phase, which may be recognised by the white colour of the crystalline solid thus formed. The product is dried at 50° C. in a recirculating air drier until reaching a constant weight. The yield of magnesium-valsartan-hexahydrate is 53.7 g or 95% based on the valsartan employed as the free acid.

The melting point for the salt hydrate produced according to example 2, namely the magnesium-valsartan-hexahydrate, for a heating rate of 10 K·min$^{-1}$ in a sealed sample container with a small internal volume, in an amount of 2.24 mg, was measured at 132° C. and the melting enthalpy at 64 kJ·Mol$^{-1}$.

The density of the crystals of the hexahydrate of the magnesium salt of valsartan produced according to example 2, determined by a helium pycnometer, is 1.273 g·cm$^{-3}$. This value conforms to the theoretically calculated value of 1.256 g·cm$^{-3}$ calculated from the single crystal structure.

The optical rotation of the magnesium-valsartan-hexahydrate produced according to example 2 is measured in methanol as a 1% solution $[\alpha]^{20}_D = -14°$.

The enantiomer purity of the salt hydrate produced according to example 2 is determined by a stereo-specific HPLC method. The stereo-specific separation is achieved by a chiral column (Chiral AGP). The enantiomer purity is determined as ee=99.6%.

Calculation of the interlattice plane intervals from the X-ray powder pattern taken with a Guinier camera is as follows for the most important lines for this batch of the magnesium valsartan hexahydrate:

d in [Å]: 19.78, 10.13, 9.84, 7.28, 6.00, 5.81, 5.67, 5.21, 5.04, 4.88, 4.21, 4.18, 4.08, 3.95, 3.46, 3.42.

Elementary analysis gives the following measured values of the elements present in the hexahydrate of the magnesium salt of valsartan and of water. The water evaluation is carried out at 130° C. after expulsion. The findings of the elementary analysis, within the error limits, correspond to the sum formula $(C_{24}H_{27}N_5O_3)^{2-}Mg^{2+}\cdot 6H_2O$.

|  | % found | % calculated |
| --- | --- | --- |
| C | 51.03 | 50.94 |
| H | 7.00 | 6.95 |
| N | 12.45 | 12.38 |
| O | 25.02 | 25.44 |
| water | 19.08 | 19.10 |
| Mg | 4.35 | 4.29 |

EXAMPLE 3

Production of the hydrate of di-potassium salt of (S)—N-(1-carboxy-2-methyl-prop-1-yl)-N-pentanoyl-N-[2'-(1H-tetrazol-5-yl)-biphenyl-4-ylmethyl]-amine (3.5±1.0 mole $H_2O$)

5 g of (S)—N-(1-carboxy-2-methyl-prop-1-yl)-N-pentanoyl-N-[2'-(1H-tetrazol-5-yl)-biphenyl-4-ylmethyl]-amine are dissolved whilst heating gently in 11.5 ml of 2 normal potassium hydroxide solution and mixed with 320 ml of acetonitrile. The mixture is heated for 5 minutes to reflux (turbid solution), left without stirring for 3 days at room temperature (seeding) and then left for 24 hours at 0° C. The mother liquor is decanted. The crystallisate is washed twice with acetonitrile and then dried in the air for 36 hours until reaching a constant weight. (S)—N-(1-carboxy-2-methyl-prop-1-yl)-N-pentanoyl-N-[2'-(1H-tetrazol-5-yl)-biphenyl-4-ylmethyl]-amine dipotassium salt hydrate is obtained (3.7 mols water per mol dipotassium salt). The melting point in a closed specimen container is 135° C.

Elementary analysis: $C_{24}H_{27}N_5O_3K_2$, $3.72H_2O$, molar mass 578.72

| | % found | % calculated |
|---|---|---|
| C | 49.90 | 49.81 |
| H | 5.92 | 6.00 |
| N | 12.14 | 12.10 |
| O | 18.55 | 18.58 |
| water | 11.58 | 11.58 |
| K | 13.50 | 13.51 |

X-ray diffraction diagram measured with the diffractometer Scintag Inc., Cupertino, Calif. 95014, US, using CuKα radiation.

Reflection lines and intensities of the most important lines of the hydrate of the di-potassium salt of valsartan, values given in 2θ in °:

| 2θ in ° | Intensity |
|---|---|
| 4.6 | strong |
| 8.8 | medium |
| 9.2 | strong |
| 11.1 | weak |
| 12.5 | weak |
| 14.8 | strong |
| 15.3 | weak |
| 16.4 | medium |
| 17.8 | strong |
| 18.2 | medium |
| 18.4 | medium |
| 18.9 | medium |
| 20.4 | medium |
| 21.1 | weak |
| 21.3 | medium |
| 22.3 | weak |
| 22.5 | strong |
| 23.1 | medium |
| 23.9 | strong |
| 25.6 | weak |
| 26.6 | strong |
| 26.9 | medium |
| 28.1 | medium |

Preferred are hydrates comprising the medium and strong intensity peaks.

TABLE 11

Crystal data and parameters of the hydrate of the di-potassium salt of valsartan Crystal data

| | |
|---|---|
| sum formula | $(C_{24}H_{27}N_5O_3)^{2-}2K^+ \cdot xH_2O$ (x = 3.5 ± 1.0) |
| molecular mass | 574.78 |
| crystal system | orthorhombic |
| space group | $P2_12_12$ |
| a (Å) | 38.555(2) |
| b (Å) | 7.577(1) |

TABLE 11-continued

Crystal data and parameters of the hydrate of the di-potassium salt of valsartan

| | |
|---|---|
| c (Å) | 10.064(1) |
| V (Å³) | 2940.0(5) |
| Z | 4 |
| F(000) | 1212 |
| $D_{calc.}$ (g·cm$^{-3}$) | 1.286 |
| number of reflections for cell parameters | 25 |
| θ range for cell parameters (°) | 30-38 |
| μ (mm$^{-1}$) | 3.24 |
| Temperature (°C.) | 23 |
| crystal shape | prisms |
| crystal size (mm) | 0.63 × 0.20 × 0.14 |
| crystal colour | colourless |
| Data collection | |
| diffractometer | Enraf Nonius CAD4 |
| radiation (graphite monochromator) | CuKα |
| wave length (Å) | 1.54178 |
| scan mode | ω/2θ |
| scan range (θ) | 3-74 |
| absorption correction | none |
| number of measured reflections | 3450 |
| number of observed reflections (I > 2σ(I)) | 2867 |
| h range | −48→0 |
| k range | −9→0 |
| l range | −12→0 |
| number of standard reflections | 3 every 120 mins |
| variation in intensity | ±5% |
| Structure refinement | |
| refinement method | refinement on F², complete matrix |
| number of parameters | 341 |
| R | 0.069 |
| $R_W$ | 0.182 |
| S | 1.57 |
| number of reflections used | 2867 |
| treatment of H-atoms | "riding", apart from those of the water molecules, which were ignored |
| $\Delta/\sigma_{max}$ | 0.24 |
| extinction correction | 0.0010(5) |
| maximum/minimum residual electron density in final difference-Fourier calculation | 0.815/−0.676(eÅ$^{-3}$) |
| absolute structure parameters | −0.02(4) |

Programmes used
SHELXS86 (Sheldrick, Göttingen),
XHELXL93 (Sheldrick, Göttingen),
SCHAKAL92 (Keller, Freiburg)

EXAMPLE 4

Production of the di-potassium salt of (S)—N-(1-carboxy-2-methyl-prop-1-yl)-N-pentanoyl-N-[2'-(1H-tetrazol-5-yl)-biphenyl-4-ylmethyl]-amine 25 g of (S)—N-(1-carboxy-2-methyl-prop-1-yl)-N-pentanoyl-N-[2'-(1H-tetrazol-5-yl)-biphenyl-4-ylmethyl]-amine are dissolved in 200 ml of ethanol. 50 ml of water are added, the solution cooled to 0° C. and then mixed with 57.4 ml of 2 normal potassium hydroxide solution. The mixture is concentrated by evaporation on a rotary evaporator, evaporated again with each of toluene and acetonitrile, and dried in a high vacuum for 15 minutes at 50° C. The product is dissolved in 290 ml of a hot mixture of acetonitrile/water (95:5), mixed with an additional 110 ml of acetonitrile, allowed to cool and seeded at ca. 30° C. The mixture is left to stand for 4 days at room temperature and filtered by suction. The residue is washed with acetonitrile/water (95:5) and dried in a high vacuum at 80° C. (S)—N-(1-carboxy-2-methyl-prop-1-yl)-N-pentanoyl-N-[2'-(1H-tetrazol-5-yl)-biphenyl-4-ylmethyl]-amine dipotassium salt is obtained as a white powder. Melting point>300° C.

Elementary analysis: The material obtained is hygroscopic and can be equilibrated in the air ($C_{24}H_{27}N_5O_3K_2$, 3.96 mols $H_2O$).

|   | % found | % calculated |
|---|---------|--------------|
| C | 49.15   | 49.44        |
| H | 6.02    | 6.04         |
| N | 11.91   | 12.01        |
| O | 19.18   | 19.1         |
| water | 12.23 | 12.24      |
| K | 13.4    | 13.41        |

EXAMPLE 5

Production of the di-sodium salt of (S)—N-(1-carboxy-2-methyl-prop-1-yl)-N-pentanoyl-N-[2'-(1H-tetrazol-5-yl)-biphenyl-4-ylmethyl]-amine 1 g of (S)—N-(1-carboxy-2-methyl-prop-1-yl)-N-pentanoyl-N-[2'-(1H-tetrazol-5-yl)-biphenyl-4-ylmethyl]-amine is dissolved in 50 ml of ethanol, mixed with 2.3 ml of 2 normal sodium hydroxide solution and concentrated by evaporation, and the residue is evaporated with each of ethanol and ethyl acetate. The white residue is stirred in hot acetonitrile and filtered by suction at room temperature. Drying in a high vacuum at 80° C. over night yields (S)—N-(1-carboxy-2-methyl-prop-1-yl)-N-pentanoyl-N-[2'-(1H-tetrazol-5-yl)-biphenyl-4-ylmethyl]-amine disodium salt as a white powder. Melting point from 260° C., brownish discolouration at 295° C.

Elementary analysis: The material obtained (hygroscopic) can be equilibrated in the air ($C_{24}H_{27}N_5O_3Na_2$, 5.36 mols $H_2O$, molar mass 576.05)

|   | % found | % calculated |
|---|---------|--------------|
| C | 49.79   | 50.04        |
| H | 6.51    | 6.60         |
| N | 12.00   | 12.16        |
| O | 23.44   | 23.22        |
| water | 16.75 | 16.76      |
| Na | 8.09   | 7.98         |

EXAMPLE 6

Production of the magnesium salt of (S)—N-(1-carboxy-2-methyl-prop-1-yl)-N-pentanoyl-N-[2'-(1H-tetrazol-5-yl)-biphenyl-4-ylmethyl]-amine 5 g of (S)—N-(1-carboxy-2-methyl-prop-1-yl)-N-pentanoyl-N-[2'-(1H-tetrazol-5-yl)-biphenyl-4-ylmethyl]-amine are added to a suspension of 0.666 g of magnesium hydroxide in 20 ml of water. 40 ml of methanol are added, then the mixture is stirred for 2 hours at room temperature and concentrated. The residue is dissolved in methanol, filtered through a hard filter, concentrated and evaporated with acetonitrile. The product is stirred with hot acetonitrile, filtered by suction at room temperature and dried in a high vacuum at 90° C. over night. (S)—N-(1-carboxy-2-methyl-prop-1-yl)-N-pentanoyl-N-[2'-(1H-tetrazol-5-yl)-biphenyl-4-ylmethyl]-amine magnesium salt is obtained as a white powder. Melting point: The sample becomes brownish upon heating and vitrifies towards 300° C.

Elementary analysis: $C_{24}H_{27}N_5O_3Mg$, 0.89 mols $H_2O$, molar mass: 473.85

|   | % found | % calculated |
|---|---------|--------------|
| C | 61.26   | 60.83        |
| H | 6.13    | 6.12         |
| N | 14.88   | 14.78        |
| O |         | 13.13        |
| water | 3.39 | 3.38         |
| Mg | 4.74   | 5.13         |

EXAMPLE 7

Production of the calcium salt of (S)—N-(1-carboxy-2-methyl-prop-1-yl)-N-pentanoyl-N-[2'-(1H-tetrazol-5-yl)-biphenyl-4-ylmethyl]-amine 5 g of (S)—N-(1-carboxy-2-methyl-prop-1-yl)-N-pentanoyl-N-[2'-(1H-tetrazol-5-yl)-biphenyl-4-ylmethyl]-amine are added to a suspension of 0.851 g of calcium hydroxide in 20 ml of water and then mixed with 200 ml of ethanol. The mixture is stirred for one hour at room temperature, concentrated by evaporation to dryness (re-evaporation with acetonitrile), stirred in hot acetonitrile (with a trace each of ethanol and water) and filtered by suction at room temperature.

0.95 g of the salt are heated to reflux in 20 ml of acetonitrile/water (1:1), whereby the mixture almost dissolves. The mixture is allowed to cool to room temperature, mixed with 20 ml of acetonitrile, filtered by suction and washed twice with acetonitrile/water (1:1) and dried over night in a high vacuum at 80° C. Melting point: from 300° C. (decomposition).

Elementary analysis: $C_{24}H_{27}N_5O_3Ca$, 1.71 mols $H_2O$, molar mass 504.39 (water evaluation carried out after expulsion at 150° C.).

|   | % found | % calculated |
|---|---------|--------------|
| C | 56.88   | 57.15        |
| H | 6.13    | 6.08         |
| N | 13.89   | 13.88        |
| O |         | 14.94        |
| water | 6.12 | 6.11         |
| Ca | 7.94   | 7.95         |

EXAMPLE 8

Production of the mono-potassium salt of (S)—N-(1-carboxy-2-methyl-prop-1-yl)-N-pentanoyl-N-[2'-(1H-tetrazol-5-yl)-biphenyl-4-ylmethyl]-amine 2 g of (S)—N-(1-carboxy-2-methyl-prop-1-yl)-N-pentanoyl-N-[2'-(1H-tetrazol-5-yl)-biphenyl-4-ylmethyl]-amine are suspended in 20 ml of water and mixed with 2.296 ml of a 2 normal potassium hydroxide solution. The mixture is stirred for 30 minutes and mixed with 50 ml of ethanol, whereupon a colourless solution is obtained. The mixture is concentrated by evaporation, evaporated once more with acetonitrile and lyophilised from tert.-butanol (with a trace of water).

Elementary analysis (after equilibration in the air). $C_{24}H_{27}N_5O_3Ca$, 1.69 mols $H_2O$, molar mass 504.06 (water evaluation carried out after expulsion at 150° C.).

| | % found | % calculated |
|---|---|---|
| C | 57.30 | 57.19 |
| H | 6.35 | 6.27 |
| N | 13.61 | 13.89 |
| O | 14.58 | 14.89 |
| water | 6.04 | 6.04 |
| K | 7.72 | 7.76 |

EXAMPLE 9

Production of the Magnesium Salt as the Hexahydrate of Valsartan by a Water-Equilibrating Process 1600 g of valsartan and 6820 g of isopropanol are stirred to form a suspension in a mixing container at room temperature, and added to an 80 liter glass receptacle with a stirrer. The mixing container is rinsed with 3919 g of isopropanol in portions and the rinsing solution added to the main mixture. After adding 3800 g of deionised water, the mixture is transformed into a homogeneous solution by stirring. Then, 156.3 g of magnesium oxide, suspended in 1520 g of deionised water, are added and the suspension supplemented with 1000 g of deionised water. By slowly stirring at room temperature, the magnesium oxide goes into solution. The pH value of the resulting solution is ca. 7.2. By adding a further 2.5 g of magnesium oxide in small portions, the pH value is raised to ca. 8.3. The resulting mixture is turbid owing to undissolved particles of unknown type in the magnesium oxide.

This mixture is transferred through a candle filter to a 35 liter enamel boiler and the glass receptacle and the transfer tube are rinsed with 885 g of isopropanol and 1122 g of deionised water. For mild concentration, a vacuum is created in the boiler to an initial theoretical value of 89-100 mbar. With a temperature of the heating medium of 45-50° C. and a boiling temperature of the mixture of 37-40° C., a total of 13.66 kg of aqueous isopropanol is distilled. By lowering the distillation pressure to a final value of 10 mbar and simultaneously raising the heating medium temperature to 65° C., the amount of distillate is increased to a total of 17.12 kg. 9300 g of ethyl acetate, followed by 14.9 g of valsartan Mg salt hexahydrate as seeding crystals, are added to the boiler content whilst stirring. Finally, a further 6680 g of ethyl acetate are dispensed in and cooling is effected to room temperature whilst stirring. The stirring procedure is maintained for at least 24 hours. The suspension is then filtered through Büchner filters. A moist filter cake is thus obtained. The boiler is rinsed with 1171 g of ethyl acetate and the rinsing mixture is used to wash the filter cake. Drying of a partial amount on metal sheets in a vacuum drying chamber at 50 mbar pressure and 40° C. oven temperature for 6.5 hours until reaching a constant weight yields a dry substance.

The physical data, especially the X-ray powder pattern, correspond to the magnesium hexahydrate salt of example 2.

EXAMPLE 10

Production of the Calcium Salt of Valsartan as the Tetrahydrate 1600 g of valsartan and 7000 g of ethanol are stirred to form a suspension in a mixing container at room temperature, and added to a 35 liter enamel boiler with a stirrer. The mixing container is rinsed with 2000 g of ethanol in portions and the rinsing solution added to the main mixture. After adding 9000 g of deionised water, the mixture is transformed into a homogeneous solution by stirring. Then, 272 g of calcium hydroxide, suspended in 1500 g of deionised water, are added and the suspension supplemented with 1300 g of deionised water. By slowly stirring at room temperature, the calcium hydroxide goes into solution. The pH value of the resulting solution is ca. 6.9. By adding a further 9.6 g of calcium hydroxide, the pH value is raised to ca. 10.6. The resulting mixture is turbid owing to undissolved particles (calcium carbonate) in the calcium hydroxide. This mixture is transferred through a candle filter to a 35 liter enamel boiler and the glass receptacle and the transfer tube are rinsed with a solution of 1048 g of ethanol and 1000 g of deionised water. For mild concentration, a vacuum is created in the boiler to a theoretical value of 100-120 mbar. With a temperature of the heating medium of ca. 50° C. and a boiling temperature of the mixture of max. 44° C., a total of 11.32 kg of aqueous ethanol is distilled. The dissolved salt crystallises spontaneously during the course of distillation. The suspension present at the end of distillation is cooled to ca. 5° C. whilst stirring, and is stirred for ca. 16 hours at 5° C. The suspension is then filtered through Büchner filters. The boiler is rinsed with a mixture of 3600 ml of deionised water and 400 ml of ethanol, the mixture being cooled to 5° C., and the rinsing mixture is used to wash the filter cake. A moist filter cake is thus obtained. Drying of a partial amount on metal sheets in a vacuum drying chamber at 50 mbar pressure and 40° C. oven temperature for 24 hours until reaching a constant weight yields a dry substance.

The physical data, especially the X-ray powder pattern, correspond to the calcium tetrahydrate salt of example 1.

EXAMPLE 11

Hydrate of Valsartan Disodium Salt (2.4±1.0 mole $H_2O$)

50 ml of 2N sodium hydroxide solution are added dropwise at ca. 25° C. to a solution of 21.5 g of valsartan in 200 ml of isopropanol. The clear solution (pH ca. 7.2) is concentrated under vacuum at ca. 40° C. The amorphous residue of the disodium salt is suspended in 100 ml of isopropanol, and water is removed by concentrating under vacuum once more at ca. 40° C. and degassing. The amorphous residue is suspended in 75 ml of acetone and 2 ml of water at ca. 40° C. At ca. 25-30° C., 200 ml of tert.-butylmethylether is added, whereby constituents that are initially smeary are gradually transformed into a crystalline suspension. After stirring over night at ca. 25° C., the suspension is cooled to 10° C. and after ca. 1 hour is filtered by suction whilst excluding atmospheric moisture. Washing then takes place with 20 ml of tert.-butylmethylether. The moist filter cake is dried over night at ca. 30 mbar and at 30° C. A colourless, slightly hygroscopic crystal powder is obtained.

Elementary analysis: $C_{24}H_{27}N_5O_3Na_2$, 2.44 mols $H_2O$

| | % found | % calculated |
|---|---|---|
| C | 55.03 | 55.07 |
| H | 6.16 | 6.14 |
| N | 13.38 | 13.38 |
| O | | 16.63 |
| water | 8.40 | 8.41 |
| Na | 8.67 | 8.78 |

X-ray diffraction diagram (reflection lines and intensities of the most important lines) of the crystalline hydrate of the disodium salt of valsartan measured with the diffractometer Scintag Inc. Cupertino, Calif. 95014, US, using CuKα radiation:

| 2θ | Intensity |
| --- | --- |
| 4.7 | strong |
| 9.1 | strong |
| 13.3 | weak |
| 13.7 | weak |
| 15.6 | medium |
| 16.4 | medium |
| 17.2 | medium |
| 17.9 | medium |
| 18.7 | medium |
| 19.6 | medium |
| 21.3 | medium |
| 21.9 | medium |
| 22.8 | strong |
| 24.0 | weak |
| 24.8 | weak |
| 25.5 | weak |
| 26.5 | medium |
| 26.8 | weak |
| 27.3 | weak |
| 27.8 | weak |
| 28.6 | weak |
| 29.4 | weak |
| 29.9 | medium |

EXAMPLE 12

Hydrate of the Valsartan Dipotassium Salt (3.4±1.0 mole H₂O)

6.9 g of potassium carbonate are added at ca. 25° C. to the solution of 21.7 g of valsartan in 150 ml of acetone and 20 ml of water. After stirring for 2 hours at ca. 25° C., an almost clear solution is obtained, which is concentrated in a vacuum at ca. 50° C. bath temperature. 55 ml of acetone are added to the residue (29.3 g) which contains residual water, and at ca. 35° C., over the course of ca. two hours, a total of 250 ml of tert.-butylmethylether is dispensed in. After stirring at ca. 25° C., the easily stirrable crystal suspension is cooled to 10° C., stirred for at least one hour, filtered by suction and washed with 20 ml of tert.butylmethylether. The moist filter cake is dried over night at ca. 30 mbar and at 30° C. A colourless, slightly hygroscopic crystal powder is obtained.

Elementary analysis: $C_{24}H_{27}N_5O_3K_2$, 3.42 mols $H_2O$

| | % found | % calculated |
| --- | --- | --- |
| C | 50.37 | 50.28 |
| H | 5.87 | 5.95 |
| N | 12.24 | 12.22 |
| O | | 17.92 |
| water | 10.76 | 10.75 |
| K | 13.4 | 13.64 |

X-ray diffraction diagram measured with the diffractometer Scintag Inc., Cupertino, Calif. 95014, US using a CuKα radiation.

Reflection lines and intensities of the most important lines of the hydrate of the di-potassium salt of valsartan, values given in 2θ in °:

| 2θ in ° | Intensity |
| --- | --- |
| 4.9 | strong |
| 9.4 | strong |
| 11.4 | weak |
| 12.8 | weak |
| 14.0 | weak |
| 15.0 | weak |
| 15.6 | weak |
| 16.6 | medium |
| 18.0 | weak |
| 18.5 | weak |
| 18.9 | weak |
| 20.7 | weak |
| 21.5 | weak |
| 22.0 | weak |
| 22.7 | medium |
| 23.3 | weak |
| 24.1 | medium |
| 25.6 | weak |
| 25.8 | weak |
| 27.1 | medium |
| 29.4 | weak |

Preferred are hydrates comprising medium and strong intensity peaks.

EXAMPLE 13

Valsartan Calcium/Magnesium Mixed Salt 21.5 g of valsartan in 200 ml of isopropanol and 100 ml of water are stirred for ca. 3 hours at ca. 25° C. with 1.5 g of magnesium hydroxide and 1.9 g of calcium hydroxide. The practically clear solution is concentrated in a vacuum at ca. 50° C. A total of 240 ml of ethyl acetate is added with stirring to the still warm, semi-solid residue which contains residual water. Upon stirring over night at ca. 25° C., initially sticky constituents are transformed into a homogeneous suspension. The suspension is filtered by suction and washed with 20 ml of ethyl acetate. The moist filter cake is dried in a vacuum at 30-40° C. A colourless crystal powder is obtained.

The X-ray diffraction diagram corresponds to a conglomerate of calcium tetrahydrate and magnesium hexahydrate from example 1 and 2.

EXAMPLE 14

Valsartan Bis-Diethylammonium Salt 1.5 g of diethylamine are added dropwise at ca. 25° C. to the solution of 4.35 g of valsartan in 60 ml of acetone. After a short time, crystallisation slowly sets in. After stirring over night, the crystallisate is filtered by suction at ca. 20° C., washed with cold acetone and dried in a vacuum at ca. 50° C. A colourless crystal powder is obtained.

Elementary analysis: $C_{32}H_{51}N_7O_3$, 0.1 mols $H_2O$

| | % found | % calculated |
| --- | --- | --- |
| C | 65.82 | 65.84 |
| H | 8.90 | 8.84 |
| N | 16.84 | 16.80 |
| O | | 8.52 |
| water | 0.34 | 0.34 |

X-ray diffraction diagram (reflection lines and intensities of the most important lines) of the crystalline bis-diethylammonium salt

| 2θ | Intensity |
|---|---|
| 4.7 | weak |
| 8.5 | strong |
| 9.3 | strong |
| 10.8 | strong |
| 11.3 | weak |
| 13.4 | strong |
| 14.0 | medium |
| 14.3 | weak |
| 14.9 | medium |
| 17.1 | medium |
| 17.4 | medium |
| 17.6 | medium |
| 18.3 | weak |
| 19.0 | medium |
| 20.0 | weak |
| 21.2 | medium |
| 21.6 | weak |
| 22.4 | medium |
| 22.7 | weak |
| 24.9 | medium |
| 25.2 | weak |
| 27.0 | weak |

EXAMPLE 15

Valsartan Bis-Dipropylammonium Salt 2.1 g of dipropylamine are added dropwise at 25° C. to the solution of 4.35 g of valsartan in 60 ml of acetone. When crystallisation has set in, the temperature is raised for a brief period to 40° C. and is allowed to drop to room temperature over ca. 2 hours. After stirring over night, the crystallisate is filtered by suction, washed twice with 15 ml of acetone and dried in a vacuum at ca. 40° C. Granular crystals are obtained.

Elementary analysis: $C_{36}H_{69}N_7O_3$, 0.05 mols $H_2O$

| | % found | % calculated |
|---|---|---|
| C | 67.74 | 67.69 |
| H | 9.32 | 9.33 |
| N | 15.36 | 15.35 |
| O | | 7.64 |
| water | 0.13 | 0.14 |

X-ray diffraction diagram (reflection lines and intensities of the most important lines) of the crystalline bis-dipropylammonium salt

| 2θ | Intensity |
|---|---|
| 8.5 | strong |
| 8.9 | weak |
| 9.4 | strong |
| 10.0 | medium |
| 11.2 | weak |
| 11.6 | weak |
| 12.5 | weak |
| 13.2 | strong |
| 13.9 | strong |
| 14.3 | weak |
| 14.7 | weak |
| 15.1 | weak |
| 15.6 | weak |
| 16.0 | weak |
| 17.0 | medium |
| 17.9 | medium |
| 18.7 | strong |
| 19.9 | weak |
| 20.4 | weak |
| 20.6 | weak |
| 21.0 | strong |
| 21.7 | weak |
| 22.3 | medium |
| 23.1 | strong |
| 24.5 | weak |
| 25.5 | medium |
| 25.8 | weak |
| 26.7 | weak |
| 28.6 | weak |

EXAMPLE 16

Bis-Dibutylammonium Salt of Valsartan

A solution of 2.15 g of valsartan in 30 ml of acetone is mixed with 1.4 g of dibutylamine at ca. 25° C. Crystallisation sets in after a short time, and the thick suspension is gradually diluted with 20 ml of isopropyl acetate over ca. 1 hour. After stirring for 4 hours at ca. 25° C., the crystals are removed by suction, washed twice with 10 ml of isopropyl acetate and dried in a vacuum at 50° C. A colourless, slightly hygroscopic crystal powder is obtained.

Elementary analysis: $C_{40}H_{67}N_7O_3$, 0.5 mols $H_2O$

| | % found | % calculated |
|---|---|---|
| C | 68.25 | 68.30 |
| H | 9.79 | 9.75 |
| N | 13.89 | 13.94 |
| O | | 8.01 |
| water | 1.33 | 1.33 |

X-ray diffraction diagram (reflection lines and intensities of the most important lines) of the crystalline bis-dibutylammonium salt

| 2θ | Intensity |
|---|---|
| 7.5 | very strong |
| 8.5 | medium |
| 9.7 | strong |
| 12.7 | strong |
| 13.3 | weak |
| 14.1 | strong |
| 15.1 | medium |
| 16.4 | strong |
| 17.7 | weak |
| 18.2 | weak |
| 19.5 | strong |
| 19.9 | medium |
| 20.5 | medium |
| 21.4 | medium |
| 21.9 | medium |
| 22.2 | medium |
| 22.6 | medium |
| 23.0 | strong |
| 23.7 | weak |
| 24.2 | weak |
| 24.7 | medium |
| 25.7 | medium |
| 26.0 | weak |
| 26.5 | weak |
| 28.8 | weak |

FORMULATION EXAMPLE 1

Directly Compressed Tablet

| No. | Ingredient | proportion per batch [g] | proportion per tablet core [mg] |
|---|---|---|---|
| 1 | valsartan calcium salt tetrahydrate | 134.24 | 80 |
| 2 | Avicel PH 102 (microcrystalline cellulose) | 60.408 | 36 |
| 3 | lactose (crystalline) | 96.1494 | 57.3 |
| 4 | crospovidone | 7.551 | 4.5 |
| 5 | aerosil 200 (silica, colloidal anhydrous) | 0.839 | 0.5 |
| 6 | magnesium stearate (vegetable) | 6.2086 | 3.7 |

Ingredient no. 1 is sieved through a 0.5 mm sieve and mixed for 15 minutes in a Turbula with ingredients 1-6. Tablets are compress using a single punch tablet press with punches of a diameter of 8 mm.

FORMULATION EXAMPLE 2

Tablet Produced by Roller Compaction

| No. | Ingredient | proportion per batch [g] | proportion per tablet core [mg] |
|---|---|---|---|
| 1 | valsartan magnesium salt hexahydrate | 400 | 80 |
| 2 | Avicel PH 102 (microcrystalline cellulose) | 270 | 54 |
| 3 | crospovidone | 75 | 15 |
| 4 | aerosil 200 (silica, colloidal anhydrous) | 7.5 | 1.5 |
| 5 | magnesium stearate | 15 | 3 |
| 6 | magnesium stearate | 7.5 | 1.5 |

Ingredients no. 1-5 are mixed for 50 minutes and compacted on a Freund roller compactor. The band is milled and after admixing ingredient no 6, compressed into tablets using a single punch tablet press with punches of a diameter of 8 mm.

What we claim is:

1. A magnesium hexahydrate salt of valsartan.

2. The hexahydrate according to claim 1, characterised by
   (i) an X-ray powder pattern taken with a Guinier camera comprising the following interlattice plane intervals: d in [A]: 19.7±0.3, 10.11±0.2, 9.8±0.2, 7.28±0.1, 5.81±0.05, 5.68±0.05, 5.03±0.05, 4.88±0.05, 4.18±0.05, 4.08±0.05, 3.46±0.05; or
   (ii) an ATR-IR spectrum having the following absorption bands expressed in reciprocal wave numbers (cm 1): 3378 (m); 3274 (m); 2956 (m); 1619 (st); 1557 (m); 1464 (m); 1419 (m); 1394 (st); 1374 (m); 1175 (m); 836 (m); 820 (s); 766 (st); 751 (m); 741 (st); 732 (st).

3. A method of treatment of diseases and conditions which can be inhibited by blocking the $AT_1$ receptor comprising administering a therapeutically effective amount of the salt of claim 1 to a patient in need thereof.

4. A pharmaceutical composition comprising the salt according to claim 1 and a pharmaceutically acceptable excipient or additive.

5. The pharmaceutical composition according to claim 4, further comprising at least one of the following:
   (i) HMG-Co-A reductase inhibitor or a pharmaceutically acceptable salt thereof,
   (ii) angiotensin converting enzyme (ACE) Inhibitor or a pharmaceutical acceptable salt thereof,
   (iii) calcium channel blocker or a pharmaceutically acceptable salt thereof,
   (iv) aldosterone synthase inhibitor or a pharmaceutical acceptable salt thereof,
   (v) aldosterone antagonist or a pharmaceutically acceptable salt thereof,
   (vi) dual angiotensin converting enzyme/neutral endopeptidase (ACE/NEP) inhibitor or a pharmaceutical acceptable salt thereof,
   (vii) endothelin antagonist or a pharmaceutical acceptable salt thereof,
   (viii) renin inhibitor or a pharmaceutical acceptable salt thereof, or
   (ix) diuretic or a pharmaceutically acceptable salt thereof.

* * * * *